(12) United States Patent
Bennani et al.

(10) Patent No.: US 7,319,103 B2
(45) Date of Patent: Jan. 15, 2008

(54) NON-IMIDAZOLE TERTIARY AMINES AS HISTAMINE 3 RECEPTOR INHIBITORS FOR THE TREATMENT OF COGNITIVE AND SLEEP DISORDERS, OBESITY AND OTHER CNS DISORDERS

(75) Inventors: Youssef L. Bennani, Shaker Heights, OH (US); James T. Anderson, Shaker Heights, OH (US); Jianmin Wang, Avon, OH (US); Michael G. Campbell, Sagamore Hills, OH (US)

(73) Assignee: Athersys, Inc., Cleveland, OH (US)

( * ) Notice: Subject to any disclaimer, the term of this patent is extended or adjusted under 35 U.S.C. 154(b) by 152 days.

(21) Appl. No.: 11/170,265

(22) Filed: Jun. 29, 2005

(65) Prior Publication Data

US 2006/0009451 A1   Jan. 12, 2006

Related U.S. Application Data

(60) Provisional application No. 60/584,795, filed on Jun. 30, 2004.

(51) Int. Cl.
```
A01N 43/54    (2006.01)
A61K 31/505   (2006.01)
C07D 239/00   (2006.01)
C07D 471/00   (2006.01)
C07D 487/00   (2006.01)
C07D 491/00   (2006.01)
```
(52) U.S. Cl. .................. 514/267; 544/250; 544/251

(58) Field of Classification Search ............ None
See application file for complete search history.

(56) References Cited

U.S. PATENT DOCUMENTS 7,034,153 B2 *  4/2006  Nakai et al. ............... 544/249

OTHER PUBLICATIONS

Bertaccini, G., et al., Review Article: the Histamine H3-receptor: a Novel Prejunctional Receptor Regulating Gastrointestinal Function, Aliment. Pharmacol. Therap. (1991) 5, 585-591.*
V. A. Makarov et al., Chemistry of Heterocyclic Compounds, vol. 34, No. 12, 1998, "Synthesis of Pyrazolo[1,5-a] Pyrimpdines by the Reaction of β-Dicarbonyl Compounds with 3,5-Diamino-4-Nitropyrazole" 1999 Kluwer Academic/Plenum Publishers.

* cited by examiner

*Primary Examiner*—James O. Wilson
*Assistant Examiner*—Erich Leeser
(74) *Attorney, Agent, or Firm*—Wood, Phillips, Katz, Clark & Mortimer

(57) ABSTRACT

This invention relates to compounds having pharmacological activity, to compositions containing these compounds, and to a method of treatment employing the compounds and compositions. More particularly, this invention concerns certain non-imidazole tertiary amine derivatives and their salts and solvates. These compounds have $H_3$ histamine receptor antagonist activity. This invention also relates to pharmaceutical compositions containing these compounds and to a method of treating disorders in which histamine $H_3$ receptor blockade is beneficial.

5 Claims, No Drawings

NON-IMIDAZOLE TERTIARY AMINES AS HISTAMINE 3 RECEPTOR INHIBITORS FOR THE TREATMENT OF COGNITIVE AND SLEEP DISORDERS, OBESITY AND OTHER CNS DISORDERS

CONTINUITY DATA

This application claims the benefit of domestic priority to U.S. provisional application 60/584,795, filed on Jun. 30, 2004.

TECHNICAL FIELD

This invention relates to compounds having pharmacological activity, to compositions containing these compounds, and to a method of treatment employing the compounds and compositions. More particularly, this invention concerns certain non-imidazole tertiary amine derivatives and their salts and solvates. These compounds alter $H_3$ histamine receptor activity. This invention also relates to pharmaceutical compositions containing these compounds and to a method of treating disorders in which histamine $H_3$ receptor blockade is beneficial.

BACKGROUND OF THE INVENTION

Histamine is a chemical messenger involved in various complex biological actions. When released, histamine interacts with specific macromolecular receptors on the cell surface or within a target cell to elicit changes in many different bodily functions. Various cell types including smooth muscle, blood cells, cells of the immune system, endocrine and exocrine cells as well as neurons respond to histamine by modulating the formation of intracellular signals, including of phosphatidylinositol, or adenylate cyclase. Evidence that histamine plays a role as a neurotransmitter was established by the mid-to-late 1970's (Schwartz, 1975) *Life Sci.* 17:503-518. Immunohistochemical studies identified histaminergic cell bodies in the tuberomammillary nucleus of the posterior hypothalamus with widespread projections in the dicencephalon and telencephalon (Inagaki et al., 1998) *J. Comp. Neurol.* 273:283-300.

Two histamine receptors ($H_1$ and $H_2$) were reported to mediate the biochemical actions of histamine on neurons. More recently, studies have demonstrated the existence of a third subtype of histamine receptor, the histamine $H_3$ receptor (Schwartz et al., 1986) *TIPS* 8: 24-28. Various studies have now demonstrated that histamine $H_3$ receptors are found on the histaminergic nerve terminals in the brains of several species, including man (Arrang et al., 1983) *Nature* 302: 832-837. The $H_3$ receptor found on the histaminergic nerve terminal was defined as an autoreceptor and could intimately control the amount of histamine released from the neurons. Histamine, the natural compound, was capable of stimulating this autoreceptor but testing of known $H_1$ and $H_2$ receptor agonists and antagonists suggested that the $H_3$ receptor has a distinct pharmacological profile. Further, $H_3$ receptors have been identified on cholinergic, serotoninergic and monoamine nerve terminals in the peripheral nervous system (PNS) and central nervous system including the cerebral cortex and cerebral vessels. These observations suggest that $H_3$ receptors are uniquely located to modulate histamine as well as other neurotransmitter release, and compounds that bind $H_3$ receptors could be important mediators of neuronal activity.

As stated, CNS histaminergic cell bodies are found in the magnocellular nuclei of the hypothalamic mammillary region and these neurons project diffusely to large areas of the forebrain. The presence of histaminergic cell bodies in the tuberomammillary nucleus of the posterior hypothalamus, a brain area involved in the maintenance of wakefulness, and their projections to the cerebral cortex suggest a role in modulating the arousal state or sleep-wake cycle. The histaminergic projection to many limbic structures such as the hippocampal formation and the amygdaloid complex suggest roles in functions such as autonomic regulation, control of emotions and motivated behaviors, and memory processes.

The concept that histamine is important for the state of arousal, as suggested by the location of histaminergic pathways, is supported by other types of evidence. Lesions of the posterior hypothalamus are well known to produce sleep. Neurochemical and electrophysiological studies have also indicated that the activity of histaminergic neurons is maximal during periods of wakefulness and is suppressed by barbiturates and other hypnotics. Intraventricular histamine induces the appearances of an arousal EEG pattern in rabbits and increased spontaneous locomotor activity, grooming and exploratory behavior in both saline and pentobarbital-treated rats.

In contrast, a highly selective inhibitor of histidine decarboxylase, the sole enzyme responsible for histamine synthesis, has been shown to impair waking in rats. These data support the hypothesis that histamine may function in modulating behavioral arousal. The role of the $H_3$ receptor in sleep-waking parameters has been demonstrated (Lin et al., 1990) *Brain Res.* 592: 325-330. Oral administration of RAMHA, a $H_3$ agonist, caused a significant increase in deep slow wave sleep in the cat. Conversely, thioperamide, a $H_3$ antagonist/inverse agonist, enhanced wakefulness in a dose-dependent fashion. Thioperamide has also been shown to increase wakefulness and decrease slow-wave and REM sleep in rats. These findings are consistent with in vivo studies demonstrating that thioperamide caused an increase in synthesis and release of histamine. Together, these data demonstrate that selective $H_3$ antagonists or inverse agonists may be useful in the treatment of arousal states and sleep disorders.

Serotonin, histamine, glutamate and acetylcholine have all been demonstrated to be diminished in the Alzheimer's (AD) brain. The histamine $H_3$ receptor has been demonstrated to regulate the release of each of these neurotransmitters. An $H_3$ receptor antagonist or inverse agonist would therefore be expected to increase the release of these neurotransmitters in the brain. Since histamine has been demonstrated to be important in arousal and vigilance, $H_3$ receptor antagonists or inverse agonists might enhance arousal and vigilance via increasing levels of neurotransmitter release and thereby improve cognition. Thus, the use of compounds that bind the use of $H_3$ receptor in AD, attention deficit disorders (ADD), age-related memory dysfunction, schizophrenia and other cognitive disorders would be supported.

$H_3$ receptor antagonists or inverse agonists may be useful in treating several other CNS disorders. It has been suggested that histamine may be involved in cerebral circulation, energy metabolism, and hypothalmic hormone secretion. For example, $H_3$ receptor antagonists or inverse agonists have been demonstrated to affect food intake and body weight gain in rodents. Recent evidence has indicated the possible use of $H_3$ antagonists or inverse agonists in the treatment of epilepsy. Work has demonstrated an inverse correlation between the duration of clonic convulsions and brain histamine levels. Thioperamide was also shown to significantly and dose-dependently decrease the durations of every convulsive phase after electrically-induced convulsions and increase the electroconvulsive threshold.

In spite of their low density, $H_3$ receptor binding sites can be detected outside the brain. Several studies have revealed the presence of $H_3$ heteroreceptors in the gastrointestinal tract, as well as upon neurons of the respitory tract. Accordingly, an $H_3$ receptor binding compound may be useful in the treatment of diseases and conditions such as asthma, rhinitis, airway congestion, inflammation, hyper and hypo motility and acid secretion of the gastrointestinal tract. Peripheral or central blockage of $H_3$ receptors may also contribute to changes in blood pressure, heart rate and cardiovascular output and could be used in the treatment of cardiovascular diseases, and in the treatment of diseases or conditions such as obesity, migraine, inflammation, motion sickness, pain, ADHD, dementia, depression, Parkinson's disease, schizophrenia, epilepsy, narcolepsy, acute myocardial infarction and asthma.

SUMMARY OF THE INVENTION

The present invention provides, in its principal aspect, compounds of the general formula:

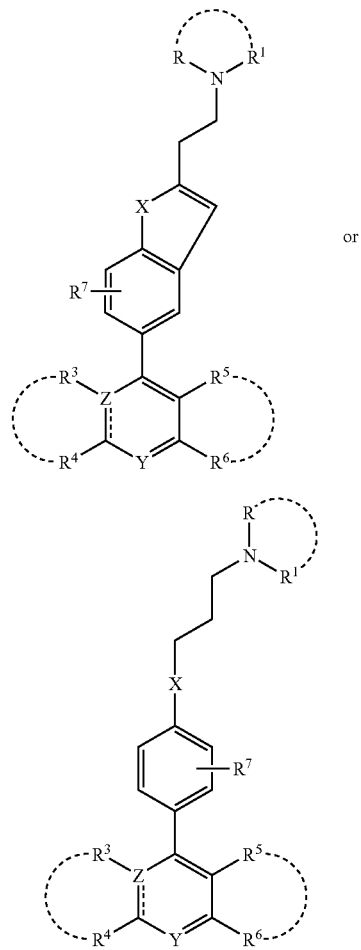

where X is O, S or $CH_2$;

Y is N or CH;
Z is N or C;
R and $R^1$ are independently:
  (C1-C8) straight or branched alkyl optionally substituted with halogens or heteroatom groups, or
  (C3-C8) cyloalkyl substituted with halogens or heteroatom groups; or
R and $R^1$ taken together form a cycloalkyl or heterocyclic group optionally substituted with:
  (C1-C8) straight or branched alkyl;
  (C3-C8) cycloalkyl;
  halogens; or
  heteroatom groups; where one or more of the methylene groups may be replaced by —O, N or S;
$R^3$ and $R^4$ taken together form:

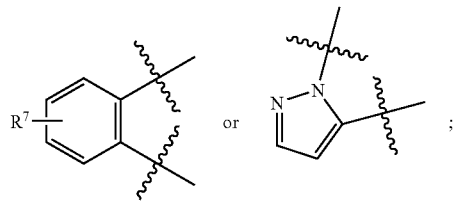

$R^5$ and $R^6$ taken together form —$(CH_2)_{3-5}$— where of one or more of the methylenes is replaced by O, N or S; and
R7 is selected from the group consisting of H, halogen, alkyl, aryl, O-alkyl, S-alkyl, NH-alkyl, N(alkyl)$_2$, acyl and N-acyl.

The pharmaceutically acceptable salts, and individual stereoisomers of compounds of structural formulae (I) and (II) above, as well as mixtures thereof, are also contemplated as falling within the scope of the present invention.

This invention also provides pharmaceutical compositions comprising a pharmaceutically acceptable carrier in combination with an effective amount of at least one compound of formulae (I) and (II).

The present invention also provides a method of treating conditions in which modulation of histamine $H_3$ receptors may be of therapeutic importance such as inflammation, migraine, motion sickness, pain, Parkinson's Disease, epilepsy, cardiovascular disease (i.e. hyper or hypotension, acute myocardial infarction), gastrointestinal disorders (acid secretion, motility) and CNS disorders involving attention or cognitive disorders (i.e., Alzheimer's, Attention Deficit Disorder, age-related memory dysfunction, stroke, etc.), psychiatric disorders (i.e., depression, schizophrenia, obsessive-compulsive disorders, etc.); sleep disorders (i.e. narcolepsy, sleep apnea, insomnia, disturbed biological and circadian rhythms, hyper and hypsomnolence), and disorders such as obesity, anorexia/bulimia, thermoregulation, hormone release) comprising administering an effective amount of a compound of formulae (I) or (II) to a patient in need of such treatment.

DETAILED DESCRIPTION OF THE INVENTION

Preferably for compounds of formulae (I) or (II), X is O, Y is N, Z is N or C,
R and $R^1$ are —$(CH_2)_3$—, —$CH_2$—$CH_2CH(CH_3)$— or —$CH_2CH_2OCH_2CH_2$—, $R^3$ and $R^4$ are

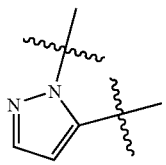

and $R^5$ and $R^6$ are —$(CH_2)_{3-5}$—, —$CH_2OCH_2$ or —$CH_2CH_2CH(CH_3)$—.

Presently preferred compounds include:

10-[4-(3-Piperidin-1-yl-propoxy)-phenyl]-6,7,8,9-tetrahydro-5H-1,4,10a-triaza-cyclohepta[f]indene;
10-{4-[3-(2-Methyl-pyrrolidin-1-yl)-propoxy]-phenyl}-6,7,8,9-tetrahydro-5H-1,4,10a-triaza-cyclohepta[f]indene;
Furan-2-ylmethyl-methyl-{3-[4-(6,7,8,9-tetrahydro-5H-1,4,10a-triaza-cyclohepta[f]inden-10-yl)-phenoxy]-propyl}-amine;
Diethyl-{3-[4-(6,7,8,9-tetrahydro-5H-1,4,10a-triaza-cyclohepta[f]inden-10-yl)-phenoxy]-propyl}-amine;
(2-Methoxy-ethyl)-{3-[4-(6,7,8,9-tetrahydro-5H-1,4,10a-triaza-cyclohepta[f]inden-10-yl)-phenoxy]-propyl}-amine;
10-[3-(3-Pyrrolidin-1-yl-propoxy)-phenyl]-6,7,8,9-tetrahydro-5H-1,4,10a-triaza-cyclohepta[f]indene;
(2-Methoxy-ethyl)-{3-[3-(6,7,8,9-tetrahydro-5H-1,4,10a-triaza-cyclohepta[f]inden-10-yl)-phenoxy]-propyl}-amine;
Furan-2-ylmethyl-{3-[3-(6,7,8,9,9a,10-hexahydro-5H-1,4,10a-triaza-cyclohepta[f]inden-10-yl)-phenoxy]-propyl}-methyl-amine;
Diethyl-{3-[3-(6,7,8,9-tetrahydro-5H-1,4,10a-triaza-cyclohepta[f]inden-10-yl)-phenoxy]-propyl}-amine;
10-[3-(3-Piperidin-1-yl-propoxy)-phenyl]-6,7,8,9-tetrahydro-5H-1,4,10a-triaza-cyclohepta[f]indene;
10-{3-[3-(2-Methyl-pyrrolidin-1-yl)-propoxy]-phenyl}-6,7,8,9-tetrahydro-5H-1,4,10a-triaza-cyclohepta[f]indene;
9-[4-(3-Pyrrolidin-1-yl-propoxy)-phenyl]-5,6,7,8-tetrahydro-pyrazolo[5,1-b]quinazoline;
9-[4-(3-Morpholin-4-yl-propoxy)-phenyl]-5,6,7,8-tetrahydro-pyrazolo[5,1-b]quinazoline;
Dimethyl-{3-[4-(5,6,7,8-tetrahydro-pyrazolo[5,1-b]quinazolin-9-yl)-phenoxy]-propyl}-amine;
9-[4-(3-Piperidin-1-yl-propoxy)-phenyl]-5,6,7,8-tetrahydro-pyrazolo[5,1-b]quinazoline;
9-{4-[3-(2-Methyl-pyrrolidin-1-yl)-propoxy]-phenyl}-5,6,7,8-tetrahydro-pyrazolo[5,1-b]quinazoline;
10-{4-[3-(2-Methyl-pyrrolidin-1-yl)-propoxy]-phenyl}-6,7,8,9-tetrahydro-5H-1,4,10a-triaza-cyclohepta[f]indene;
8-[4-(3-Pyrrolidin-1-yl-propoxy)-phenyl]-6,7-dihydro-5H-1,4,8a-triaza-s-indacene;
8-[4-(3-Morpholin-4-yl-propoxy)-phenyl]-6,7-dihydro-5H-1,4,8a-triaza-s-indacene;
{3-[4-(6,7-Dihydro-5H-1,4,8a-triaza-s-indacen-8-yl)-phenoxy]-propyl}-dimethyl-amine;
8-[4-(3-Piperidin-1-yl-propoxy)-phenyl]-6,7-dihydro-5H-1,4,8a-triaza-s-indacene;
8-{4-[3-(2-Methyl-pyrrolidin-1-yl)-propoxy]-phenyl}-6,7-dihydro-5H-1,4,8a-triaza-s-indacene;
8-{4-[3-(2-Methyl-pyrrolidin-1-yl)-propoxyl]-phenyl}-5H,7H-6-oxa-1,4,8a-triaza-s-indacene;
10-{4-[3-(2,5-Dimethyl-pyrrolidin-1-yl)-propoxy]-phenyl}-6,7,8,9-tetrahydro-5H-1,4,10a-triaza-cyclohepta[f]indene;
9-{4-[3-(2-Methyl-pyrrolidin-1-yl)-propoxy]-phenyl}-5,6,7,8-tetrahydro-pyrazolo[5,1-b]quinazoline;
11-[4-(3-Pyrrolidin-1-yl-propoxy)-phenyl]-7,8,9,10-tetrahydro-6H-cyclohepta[b]quinoline;
9-[4-(3-Pyrrolidin-1-yl-propoxy)-phenyl]-1,2,3,4-tetrahydro-acridine;
9-{2-[2-(2-Methyl-pyrrolidin-1-yl)-ethyl]-benzofuran-5-yl}-5,6,7,8-tetrahydro-pyrazolo[5,1-b]quinazoline;
8-[2-(2-Pyrrolidin-1-yl-ethyl)-benzofuran-5-yl]-6,7-dihydro-5H-1,4,8a-triaza-s-indacene;
8-[2-(2-Morpholin-4-yl-ethyl)-benzofuran-5-yl]-6,7-dihydro-5H-1,4,8a-triaza-s-indacene;
8-[2-(2-Piperidin-1-yl-ethyl)-benzofuran-5-yl]-6,7-dihydro-5H-1,4,8a-triaza-s-indacene;
8-{2-[2-(2-Methyl-pyrrolidin-1-yl)-ethyl]-benzofuran-5-yl}-6,7-dihydro-5H-1,4,8a-triaza-s-indacene;
9-[2-(2-Piperidin-1-yl-ethyl)-benzofuran-5-yl]-5,6,7,8-tetrahydro-pyrazolo[5,1-b]quinazoline;
9-[2-(2-Morpholin-4-yl-ethyl)-benzofuran-5-yl]-5,6,7,8-tetrahydro-pyrazolo[5,1-b]quinazoline; and
9-{2-[2-(2-Methyl-pyrrolidin-1-yl)-ethyl]-benzofuran-5-yl}-5,6,7,8-tetrahydro-pyrazolo[5,1-b]quinazoline.

Particularly preferred compounds include:

9-[4-(3-Morpholin-4-yl-propoxy)-phenyl]-5,6,7,8-tetrahydro-pyrazolo[5,1-b]quinazoline;
10-{4-[3-(2-Methyl-pyrrolidin-1-yl)-propoxy]-phenyl}-6,7,8,9-tetrahydro-5H-1,4,10a-triaza-cyclohepta[f]indene;
8-[4-(3-Pyrrolidin-1-yl-propoxy)-phenyl]-6,7-dihydro-5H-1,4,8a-triaza-s-indacene;
8-[4-(3-Piperidin-1-yl-propoxy)-phenyl]-6,7-dihydro-5H-1,4,8a-triaza-s-indacene;
8-{4-[3-(2-(R)-Methyl-pyrrolidin-1-yl)-propoxy]-phenyl}-6,7-dihydro-5H-1,4,8a-triaza-s-indacene;
9-{4-[3-(2-(R)-Methyl-pyrrolidin-1-yl)-propoxy]-phenyl}-5,6,7,8-tetrahydro-pyrazolo[5,1-b]quinazoline;
9-[4-(3-Piperidin-1-yl-propoxy)-phenyl]-5,6,7,8-tetrahydro-pyrazolo[5,1-b]quinazoline;
8-{4-[3-(2-(R)-Methyl-pyrrolidin-1-yl)-propoxy]-phenyl}-6,7-dihydro-5H-1,4,8a-triaza-s-indacene; and
8-{4-[3-(2-Methyl-pyrrolidin-1-yl)-propoxy]-phenyl}-5H,7H-6-oxa-1,4,8a-triaza-s-indacene;

Certain compounds of the invention may exist in different isomeric (e.g. enantiomers and distereoisomers) forms. The invention contemplates all such isomers both in pure form and in a mixture, including racemic mixtures. Enol and tautomeric forms are also included.

The compounds of the invention can exist in unsolvated as well as solvated forms, including hydrated forms, e.g., hemi-hydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide, potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.,* 66: 1-19 (1977) which is incorporated herein by reference.

As throughout this specification and appended claims, the following terms have the meanings ascribed to them:

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "cycloalkyl" as used herein refers to an aliphatic ring system having 3 to 10 carbon atoms and 1 to 3 rings, including, but not limited to cyclopropyl, cyclopentyl, cyclohexyl, norbornyl, and adamantly among others. Cycloalkyl groups can be unsubstituted or substituted with one, two or three substituents independently selected from lower alkyl, haloalkyl, alkoxy, thioalkoxy, amino, alkylamino, dialkylamino, hydroxyl, halo, mercapto, nitro, carboxaldehyde, carboxy, alkoxycarbonyl and carboximide.

"Cycloalkyl" includes cis or trans forms. Furthermore, the substituents may either be in endo or exo positions in the bridged bicyclic systems.

The term "halo" or "halogen" as used herein refers to I, Br, Cl or F.

The term "heteroatom" as used herein refers to at least one N, O or S atom.

The term "heterocyclyl" as used herein, alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, triflouromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. *Pharmaceutical Sciences,* 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; (f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

Compounds of the present invention that are formed by in vivo conversion of a different compound that was administered to a mammal are intended to be included within the scope of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The invention may be illustrated by the following representative schemes and examples.

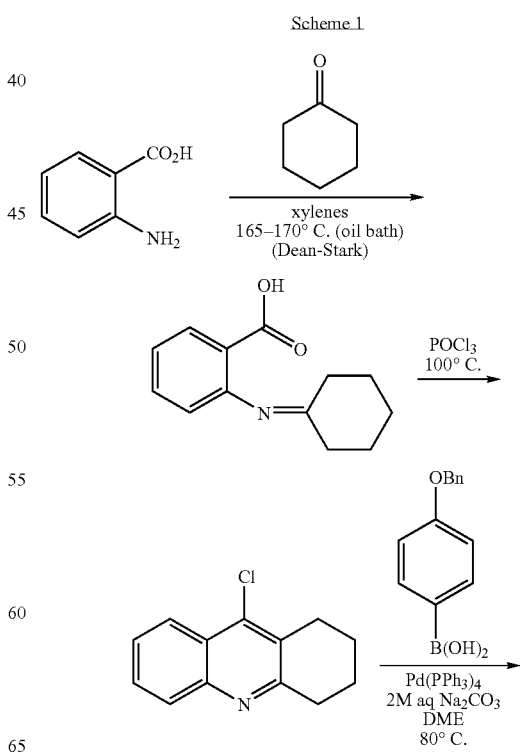

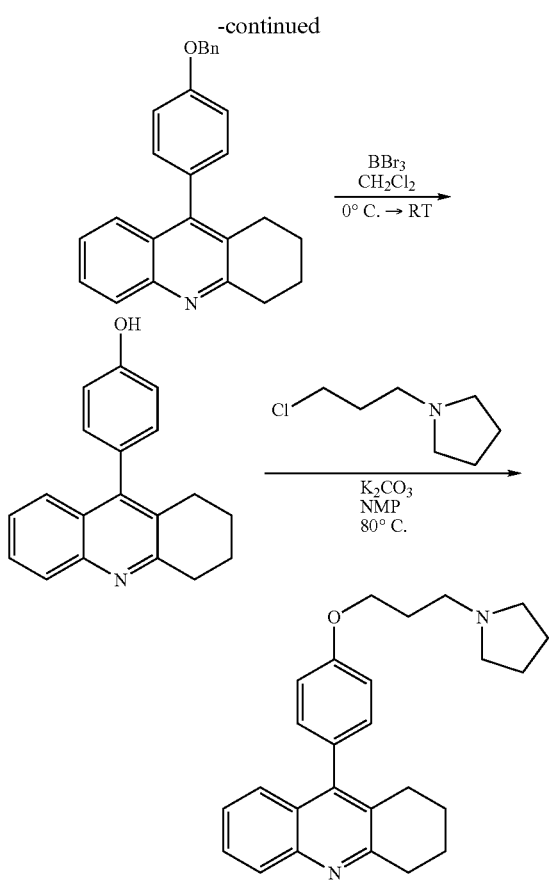

EXAMPLE 1

2-Cyclohexylideneamino-benzoic acid

Anthranilic acid (10 g, 73 mmol) and cyclohexanone (9.8 mL, 95 mmol) were dissolved in xylenes (110 mL) in a flask equipped with a Dean-Stark apparatus and heated to reflux over 18 hours. The reaction mixture was cooled to room temperature and the resulting precipitate collected by filtration. The filter cake was washed with hexanes and dried in vacuo to give the desired imine (11 g, 69% yield) as a beige solid.

LC-Mass (ES): [M+1]$^+$ calc'd for $C_{13}H_{16}NO_2$, 218; found, 218.

9-Chloro-1,2,3,4-tetrahydro-acridine

2-Cyclohexylideneamino-benzoic acid (1.5 g, 6.9 mmol) was added to phosphorus oxychloride (4 mL) at 0° C. and stirred for 5 minutes followed by heating to 100° C. for 45 minutes. The reaction mixture was cooled to room temperature and slowly poured onto ice (~100 g) and stirred for 30 minutes. CH$_2$Cl$_2$ (100 mL) was added and the mixture stirred for 5 minutes and the organic layer separated. The aq. layer was extracted with CH$_2$Cl$_2$ (50 mL). The combined CH$_2$Cl$_2$ layers were washed with sat. aq. NaHCO$_3$ (2×50 mL), sat. aq. NaCl (50 mL), dried over Na$_2$SO$_4$, decanted and concentrated to give 9-chloro-1,2,3,4-tetrahydro-acridine, which was used without further purification.

LC-Mass (ES): [M+1]$^+$ calc'd for $C_{13}H_{13}ClN$, 218; found, 218.

9-(4-Benzyloxy-phenyl)-1,2,3,4-tetrahydro-acridine

A mixture of 9-chloro-1,2,3,4-tetrahydro-acridine (282 mg, 1.30 mmol), 4-Benzyloxyphenyl boronic acid (443 mg, 1.94 mmol), tetrakistriphenylphosphine palladium (15 mg, 0.01 mmol), and 2 M aq Na$_2$CO$_3$ (0.97 mL, 1.94 mmol) was heated to 80° C. in 1,2-dimethoxyethane (2 mL) with vigorous stirring overnight in a sealed vial. The reaction mixture was cooled to room temperature and partitioned between EtOAc (50 mL) and H$_2$O (10 mL). The aq. layer was extracted with EtOAc (25 mL). The combined organic layers were washed with sat. aq. NaCl (25 mL), dried over Na$_2$SO$_4$, filtered, and concentrated. The residue was triturated with hexanes (50 mL) and to give a mixture of the desired product and starting chloride, which was used without further purification.

LC-Mass (ES): [M+1]$^+$ calc'd for $C_{26}H_{24}NO$, 366; found, 366.

4-(1,2,3,4-Tetrahydro-acridin-9-yl)-phenol

BBr$_3$ (3.2 mL, 1 M solution in CH$_2$Cl$_2$, 3.2 mmol) was added dropwise to a stirred solution of 9-(4-benzyloxy-phenyl)-1,2,3,4-tetrahydro-acridine (0.23 g 0.64 mmol) in CH$_2$Cl$_2$ (3 mL) at 0° C. The resulting mixture was warmed to room temperature over a period of 3 hours followed by dilution with CH$_2$Cl$_2$ (50 mL). The solution was washed with sat. aq. NaHCO$_3$ until aq. washings were basic (pH~9). The CH$_2$Cl$_2$ layer was dried over Na$_2$SO$_4$, decanted and concentrated. The residue was washed with hexanes (2×10 mL) and decanted to remove benzyl bromide. The resulting product was used without further purification.

LC-Mass (ES): [M−1]$^−$ calc'd for $C_{19}H_{16}NO$, 274; found, 274.

9-[4-(3-Pyrrolidin-1-yl-propoxy)-phenyl]-1,2,3,4-tetrahydro-acridine

The product from the previous step, 4-(1,2,3,4-Tetrahydro-acridin-9-yl)-phenol (22 mg, 0.08 mmol), 1-(3-Chloropropyl)-pyrrolidine (18 mg, 0.12 mmol), and K$_2$CO$_3$ (17 mg, 0.12 mmol) were mixed in NMP (267 uL) and stirred rapidly at 80° C. for 90 minutes in a sealed vial. The reaction mixture was cooled, partitioned between Et$_2$O (50 mL) and H$_2$O (10 mL). The organic layer was washed with H$_2$O (3×10 mL), sat. aq. NaCl (10 mL), dried over Na$_2$SO$_4$, decanted and concentrated. The residue was purified using preparative LCMS to give product the desired product.

LC-Mass (ES): [M+1]$^+$ calc'd for $C_{26}H_{31}N_2O$, 387; found, 387. $^1$H NMR (CDCl$_3$, 300 MHz): δ 8.00 (d, J=8.5 Hz, 1H), 7.54-7.63 (m, 1H), 7.28-7.40 (m, 2H), 7.14 (d, J=8.5 Hz, 2H), 7.04 (d, J=8.5 Hz, 2H), 4.12 (d, J=6.4 Hz, 2H), 3.19 (d, J=6.6 Hz, 2H), 2.70-2.80 (m, 2H), 2.51-2.70 (m, 4H), 1.67-2.03 (m, 12H)

Scheme 2

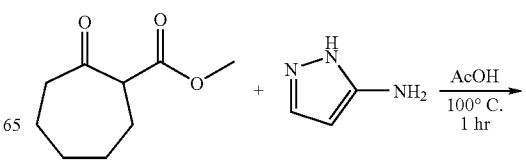

-continued

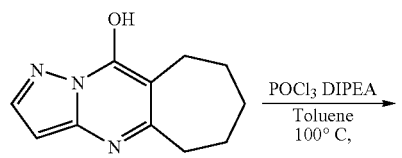

POCl₃ DIPEA
Toluene
100° C,

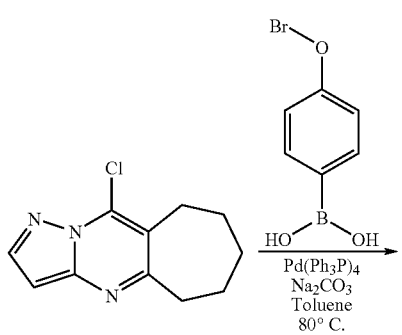

Pd(Ph₃P)₄
Na₂CO₃
Toluene
80° C.

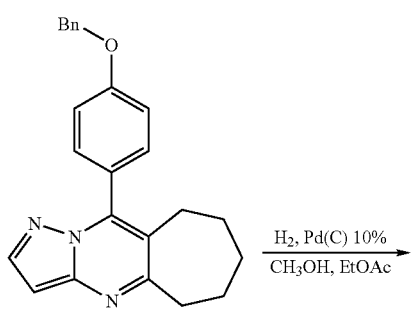

H₂, Pd(C) 10%
CH₃OH, EtOAc

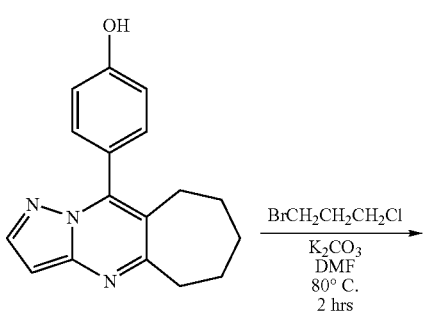

BrCH₂CH₂CH₂Cl
K₂CO₃
DMF
80° C.
2 hrs

-continued

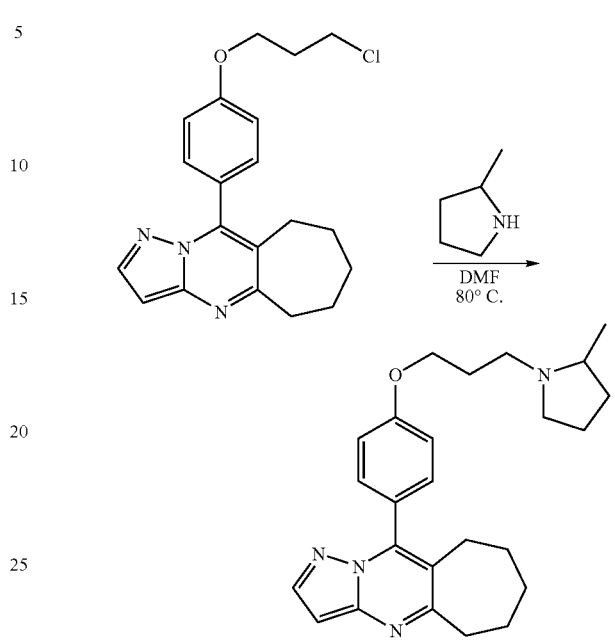

EXAMPLE 2

6,7,8,9-Tetrahydro-5H-1,4,10a-triaza-cyclohepta[f]inden-10-ol

A solution of 2-oxo-cycloheptanecarboxylic acid methyl ester (5 g, 29.4 mmol) and 2H-pyrazol-3-ylamine (2.44 g, 29.4 mmol) in acetic acid (5 mL) was heated at 100° C. for 1 hour and resulted in the formation of a colorless precipitate. The solid was collected via filtration and washed with ethanol and ethyl ether to give 6,7,8,9-tetrahydro-5H-1,4,10a-triaza-cyclohepta[f]inden-10-ol (5 g, 85% yield). The product was used without further purification.

LC-Mass (ES): [M+1]⁺ calc'd for $C_{11}H_{14}N_3O$, 204; found, 204. ¹H-NMR (DMSO-d₆, 300 MHz): δ 7.81 (d, J=0.8, 1H), 6.05 (d, J=0.8, 1H), 2.77-2.69 (m, 4H), 1.79-1.75 (m, 2H), 1.67-1.63 (m, 2H), 1.50-1.47 (m, 2H).

10-Chloro-6,7,8,9-tetrahydro-5H-1,4,10a-triaza-cyclohepta[f]indene

To a suspension of 6,7,8,9-tetrahydro-5H-1,4,10a-triaza-cyclohepta[f]inden-10-ol (5 g, 29.4 mmol) in toluene (20 mL) was added phosphorus oxychloride (37 g, 246 mmol) and diisopropylethylamine (3.1 g, 24.6 mmol). The mixture was heated to reflux for 40 min then cooled to room temperature. The product crystallized from the reaction mixture on standing over a two-day period at room temperature. The solid was collected and washed with ether to give 10-chloro-6,7,8,9-tetrahydro-5H-1,4,10a-triaza-cyclohepta[f]indene (2.3 g, 42.5% yield). The product was used without further purification.

LC-Mass (ES): [M+1]⁺ calc'd for $C_{11}H_{13}ClN_3$, 222; found, 222. ¹H-NMR (DMSO-d₆, 300 MHz): δ 8.21 (d, J=0.7, 1H), 6.70 (d, J=0.7, 1H), 3.07-2.99 (m, 4H), 1.82-1.78 (m, 2H), 1.70-1.69 (m, 4H).

10-(4-Benzyloxy-phenyl)-6,7,8,9-tetrahydro-5H-1,4,10a-triaza-cyclohepta[f]indene To a solution of 10-chloro-6,7,8,9-tetrahydro-5H-1,4,10a-triaza-cyclohepta[f]indene (221 mg, 1.0 mmol) in toluene (4 mL) was added 4-benzyloxyphenyl boronic acid (100 mg, 2.0 mmol), tetrakis(triphenylphosphine) palladium (5.7 mg, 0.0047 mmol), and 2M aq $Na_2CO_3$ (1.0 mL, 2.0 mmol). The reaction was flushed with argon and stirred at 80° C. overnight. The solution was cooled, followed by dilution with EtOAc (3 mL). The organic layer was washed with $H_2O$, brine, dried over $MgSO_4$, and concentrated. The residue was purified via flash chromatography (5-30% EtOAc/Hexane) to provide 10-(4-benzyloxy-phenyl)-6,7,8,9-tetrahydro-5H-1,4,10a-triaza-cyclohepta[f]indene (200 mg, 54% yield).

LC-Mass (ES): $[M+1]^+$ calc'd for $C_{24}H_{24}N_3O$, 370; found: 370. $^1$H-NMR (CDCl$_3$, 300 MHz): δ 7.96 (m, 1H), 7.48-7.36 (m, 7H), 7.20 (d, J=8.8 Hz, 2H), 6.55-6.59 (m, 1H), 5.12 (s, 2H), 3.11 (t, J=4.0 Hz, 2H), 2.68 (t, J=5.3 Hz, 1.82-1.86 (m, 4H), 1.68-1.61(m, 2H).

4-(6,7,8,9-Tetrahydro-5H-1,4,10a-triaza-cyclohepta[f]inden-10-yl)-phenol 10-(4-Benzyloxy-phenyl)-6,7,8,9-tetrahydro-5H-1,4,10a-triaza-cyclohepta[f]indene (100 mg, 0.27 mmol) was dissolved in $CH_3OH$ (5 mL) and EtOAc (2 mL) followed by the addition of palladium (10% by weight on carbon, 5 mg). The resulting mixture was stirred under a hydrogen atmosphere (balloon) at room temperature overnight. The catalyst was filtered off and the filtrate concentrated to give 4-(6,7,8,9-tetrahydro-5H-1,4,10a-triaza-cyclohepta[f]inden-10-yl)-phenol as a colorless solid (60 mg, 79% yield).

LC-Mass (ES): $[M+1]^+$ calc'd for $C_{17}H_{18}N_3O$, 280; found: 280. $^1$H-NMR (CDCl$_3$, 300 MHz): δ 7.94 (s, 1H), 7.29 (d, J=8.8 Hz, 2H), 7.01 (d, J=8.8 Hz, 2H), 6.57 (s, 1H), 3.11 (t, J=4.0, 6.3, 2H), 2.70 (t, J=3.0, 5.3 Hz, 2H), 1.88-1.85 (m, 4H), 1.69-1.66 (m, 2H).

10-[4-(3-Chloro-propoxy)-phenyl]-6,7,8,9-tetrahydro-5H-1,4,10a-triaza-cyclohepta[f]indene To a solution of 4-(6,7,8,9-tetrahydro-5H-1,4,10a-triaza-cyclohepta[f]inden-10-yl)-phenol (60 mg, 0.2 mmol) in DMF (1 mL) was added 1-bromo-3-chloropropane (67 mg, 0.4 mol) and $K_2CO_3$ (45 mg, 0.3 mmol). The mixture was stirred at 80° C. for 5 hours, then cooled, diluted with EtOAc (3 mL) and washed with $H_2O$. The organic layer was washed with brine, dried over $MgSO_4$, and concentrated. The residue was purified via preparative LCMS to give 10-[4-(3-chloro-propoxy)-phenyl]-6,7,8,9-tetrahydro-5H-1,4,10a-triaza-cyclohepta[f]indene (13 mg, 32% yield).

LC-Mass (ES): $[M+1]^+$ calc'd for $C_{20}H_{23}ClN_3O$, 356; found: 356. $^1$H-NMR (CDCl$_3$, 300 MHz): δ 7.97 (s, 1H), 7.39 (d, J=8.6 Hz, 2H), 7.09 (d, J=8.6 Hz, 2H), 6.57 (s, 1H), 4.20 (t, J=4.0 Hz 2H), 3.78 (t, J=7.1 Hz, 2H), 3.11 (t, J=6.2 Hz, 2H), 2.68 (t, J=5.3 Hz, 2H), 2.38-2.24 (m, 2H), 1.84 (m, 4H), 1.72 (m, 2H).

10-{4-[3-(2-Methyl-pyrrolidin-1-yl)-propoxy]-phenyl}-6,7,8,9-tetrahydro-5H-1,4,10a-triaza-cyclohepta[f]indene A mixture of 10-[4-(3-chloro-propoxy)-phenyl]-6,7,8,9-tetrahydro-5H-1,4,10a-triaza-cyclohepta[f]indene (50 mg, 0.2 mmol), 2-methyl-pyrrolidine (71 mg, 1.0 mmol) and $K_2CO_3$ (45 mg, 0.3 mmol) in DMF (1 mL) was stirred at 80° C. overnight. The reaction was cooled, diluted with EtOAc (3 mL) and washed with $H_2O$, brine, dried over $MgSO_4$, and concentrated. The residue was purified by preparative LCMS to give 10-{4-[3-(2-methyl-pyrrolidin-1-yl)-propoxy]-phenyl}-6,7,8,9-tetrahydro-5H-1,4,10a-triaza-cyclohepta[f]indene (33 mg, 66% yield).

LC-Mass (ES): $[M+1]^+$ calc'd for $C_{25}H_{33}N_4O$, 405; found: 405. $^1$H-NMR (CDCl$_3$, 300 MHz): δ 7.95 (s, 1H), 7.34 (d, J=8.4 Hz, 2H), 7.07 (d, J=8.6 Hz, 2H), 6.57 (s, 1H), 4.13-4.08 (m, 2H), 3.29 (m, 1H), 3.13-3.04 (m, 3H), 2.68 (d, J=5.4 Hz, 2H), 2.49-2.46 (m, 1H), 2.37-2.26 (m, 2H), 2.11-2.04 (m, 2H), 2.05-1.95 (m, 1H), 1.90-1.80 (m, 6H), 1.70-1.60 (m, 2H), 1.55-1.40 (m, 1H), 1.45 (d, J=4.3 Hz, 3H). MS (ES): $[M+1]^+$ calc'd for $C_{25}H_{33}N_4O$, 405; found: 405.

EXAMPLE 3

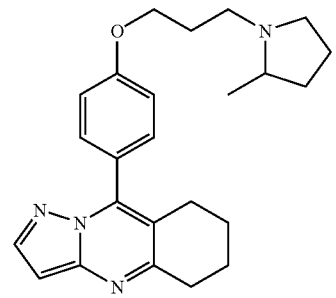

5,6,7,8-Tetrahydro-pyrazolo[5,1-b]quinazolin-9-ol

Using the method described for the preparation of 6,7,8,9-tetrahydro-5H-1,4,10a-triaza-cyclohepta[f]inden-10-ol, the reaction of 2-oxo-cyclohexanecarboxylic acid methyl ester and 2H-pyrazol-3-ylamine in acetic acid provided the title compound.

MS (ES): $[M+1]^+$ calc'd for $C_{10}H_{12}N_3O$, 190; found: 190.

9-Chloro-5,6,7,8-tetrahydro-pyrazolo[5,1-b]quinazoline

Using the method described for the preparation of 10-chloro-6,7,8,9-tetrahydro-5H-1,4,10a-triaza-cyclohepta[f]indene, the reaction of 7,8-tetrahydro-pyrazolo[5,1-b]quinazolin-9-ol and phosphorus oxychloride provided the title compound.

MS (ES): $[M+1]^+$ calc'd for $C_{10}H_{11}ClN_3$, 208; found: 208.

9-(4-Benzyloxy-phenyl)-5,6,7,8-tetrahydro-pyrazolo[5,1-b]quinazoline

Using the method described for the preparation of 10-(4-benzyloxy-phenyl)-6,7,8,9-tetrahydro-5H-1,4,10a-triaza-cyclohepta[f]indene, the reaction of 9-chloro-5,6,7,8-tetrahydro-pyrazolo[5,1-b]quinazoline and 4-benzyloxyphenyl boronic acid provided the title compound.

MS (ES): $[M+1]^+$ calc'd for $C_{23}H_{22}N_3O$, 356; found: 356.

4-(5,6,7,8-Tetrahydro-pyrazolo[5,1-b]quinazolin-9-yl)-phenol

Using the method described for the preparation of 4-(6,7,8,9-tetrahydro-5H-1,4,10a-triaza-cyclohepta[f]inden-10-yl)-phenol, (4-benzyloxy-phenyl)-5,6,7,8-tetrahydro-pyrazolo[5,1-b]quinazoline and hydrogen in the presence of 10% Pd/C provided the title compound.

MS (ES): [M+1]$^+$ calc'd for $C_{16}H_{16}N_3O$, 266; found: 266.

9-[4-(3-Chloro-propoxy)-phenyl]-5,6,7,8-tetrahydro-pyrazolo[5,1-b]quinazoline Using the method described for the preparation of 10-[4-(3-chloro-propoxy)-phenyl]-6,7,8,9-tetrahydro-5H-1,4,10a-triaza-cyclohepta[f]indene, the reaction of 4-(5,6,7,8-tetrahydro-pyrazolo[5,1-b]quinazolin-9-yl)-phenol and 1-bromo-3-chloropropane provided the title compound.

MS (ES): [M+1]$^+$ calc'd $C_{19}H_{21}ClN_3O$, 342; found: 342.

9-{4-[3-(2-Methyl-pyrrolidin-1-yl)-propoxy]-phenyl}-5,6,7,8-tetrahydro-pyrazolo[5,1-b]quinazoline Using the method described for the preparation of 10-{4-[3-(2-methyl-pyrrolidin-1-yl)-propoxy]-phenyl}-6,7,8,9-tetrahydro-5H-1,4,10a-triaza-cyclohepta[f]indene, the reaction of 9-[4-(3-chloro-propoxy)-phenyl]-5,6,7,8-tetrahydro-pyrazolo[5,1-b]quinazoline and 2-methyl-pyrrolidine provided the desired compound 9-{4-[3-(2-methyl-pyrrolidin-1-yl)-propoxy]-phenyl}-5,6,7,8-tetrahydro-pyrazolo[5,1-b]quinazoline.

MS (ES): [M+1]$^+$ calc'd $C_{24}H_{30}N_4O$, 390; found: 390.

EXAMPLE 4

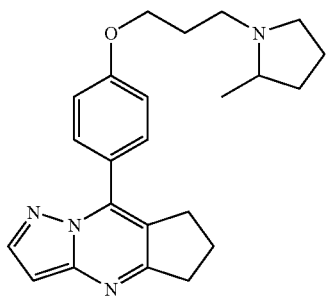

6,7-Dihydro-5H-1,4,8a-triaza-s-indacen-8-ol

Using the method described for the preparation of 6,7,8,9-tetrahydro-5H-1,4,10a-triaza-cyclohepta[f]inden-10-ol, the reaction of 2-oxo-cyclopentanecarboxylic acid methyl ester and 2H-pyrazol-3-ylamine in acetic acid provided the title compound.

MS (ES): [M+1]$^+$ calc'd for $C_9H_{10}N_3O$, 176; found: 176.

8-Chloro-6,7-dihydro-5H-1,4,8a-triaza-s-indacene

Using the method described for the preparation of 10-chloro-6,7,8,9-tetrahydro-5H-1,4,10a-triaza-cyclohepta[f]indene, the reaction of 6,7-dihydro-5H-1,4,8a-triaza-s-indacen-8-ol and phosphorus oxychloride provided the title compound.

MS (ES): [M+1]$^+$ calc'd for $C_9H_8ClN_3$, 194; found: 194.

8-(4-Benzyloxy-phenyl)-6,7-dihydro-5H-1,4,8a-triaza-s-indacene

Using the method described for the preparation of 10-(4-benzyloxy-phenyl)-6,7,8,9-tetrahydro-5H-1,4,10a-triaza-cyclohepta[f]indene, the reaction of 8-chloro-6,7-dihydro-5H-1,4,8a-triaza-s indacene and 4-benzyloxyphenyl boronic acid provided the title compound.

MS (ES): [M+1]$^+$ calc'd for $C_{22}H_{20}N_3O$, 342; found: 342.

4-(6,7-Dihydro-5H-1,4,8a-triaza-s-indacen-8-yl)-phenol

Using the method described for the preparation of 4-(6,7,8,9-tetrahydro-5H-1,4,10a-triaza-cyclohepta[f]inden-10-yl)-phenol, the reaction of 8-(4-benzyloxy-phenyl)-6,7-dihydro-5H-1,4,8a-triaza-s-indacene and hydrogen in the presence of 10% Pd/C provided the title compound.

MS (ES): [M+1]$^+$ calc'd $C_{15}H_{14}N_3O$, 252; found: 252.

8-[4-(3-Chloro-propoxy)-phenyl]-6,7-dihydro-5H-1,4,8a-triaza-s-indacene

Using the method described for the preparation of 10-[4-(3-chloro-propoxy)-phenyl]-6,7,8,9-tetrahydro-5H-1,4,10a-triaza-cyclohepta[f]indene, the reaction of 4-(6,7-dihydro-5H-1,4,8a-triaza-s-indacen-8-yl)-phenol and 1-bromo-3-chloropropane provided the title compound.

MS (ES): [M+1]$^+$ calc'd $C_{18}H_{19}ClN_3O$, 328; found: 328.

8-{4-[3-(2-Methyl-pyrrolidin-1-yl)-propoxy]-phenyl}-6,7-dihydro-5H-1,4,8a-triaza-s-indacene Using the method described for the preparation of 10-{4-[3-(2-methyl-pyrrolidin-1-yl)-propoxy]-phenyl}-6,7,8,9-tetrahydro-5H-1,4,10a-triaza-cyclohepta[f]indene, the reaction of 8-[4-(3-chloro-propoxy)-phenyl]-6,7-dihydro-5H-1,4,8a-triaza-s-indacene and 2-methyl-pyrrolidine provided the title compound.

MS (ES): [M+1]$^+$ calc'd $C_{23}H_{29}N_4O$, 377; found: 377.

EXAMPLE 5

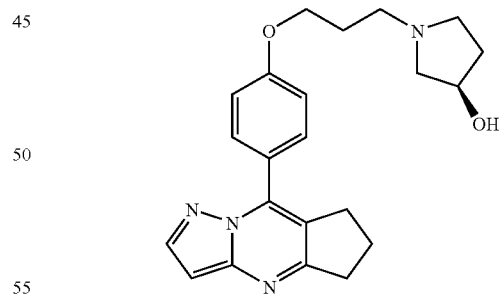

1-{3-[4-(6,7-Dihydro-5H-1,4,8a-triaza-s-indacen-8-yl)-phenoxy]-propyl}-pyrrolidin-3-(R)-ol Using the method described for the preparation of 10-{4-[3-(2-methyl-pyrrolidin-1-yl)-propoxy]-phenyl}-6,7,8,9-tetrahydro-5H-1,4,10a-triaza-cyclohepta[f]indene, the reaction of 8-[4-(3-chloro-propoxy)-phenyl]-6,7-dihydro-5H-1,4,8a-triaza-s-indacene and 3-(R)-hydroxy-pyrrolidine provided the title compound.

MS (ES): [M+1]$^+$ calc'd $C_{22}H_{27}N_4O_2$, 379; found: 379.

EXAMPLE 6

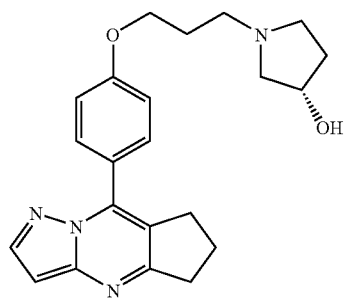

1-{3-[4-(6,7-Dihydro-5H-1,4,8a-triaza-s-indacen-8-yl)-phenoxy]-propyl}-pyrrolidin-3-(S)-ol Using the method described for the preparation of 10-{4-[3-(2-methyl-pyrrolidin-1-yl)-propoxy]-phenyl}-6,7,8,9-tetrahydro-5H-1,4,10a-triaza-cyclohepta[f]indene, the reaction of 8-[4-(3-chloro-propoxy)-phenyl]-6,7-dihydro-5H-1,4,8a-triaza-s-indacene and 3-(S)-hydroxy-pyrrolidine provided the title compound.

MS (ES): [M+1]$^+$ calc'd $C_{22}H_{27}N_4O_2$, 379; found: 379.

EXAMPLE 7

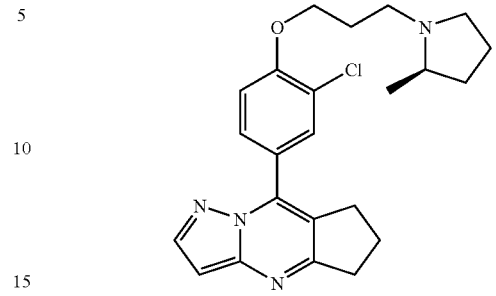

8-{3-Chloro-4-[3-(2-(R)-methyl-pyrrolidin-1-yl)-propoxy]-phenyl}-6,7-dihydro-5H-1,4,8a-triaza-s-indacene Using the method described for the preparation of 10-{4-[3-(2-Methyl-pyrrolidin-1-yl)-propoxy]-phenyl}-6,7,8,9-tetrahydro-5H-1,4,10a-triaza-cyclohepta[f]indene, the reaction of 8-[(3-chloro)-4-(3-chloro-propoxy)-phenyl]-6,7-dihydro-5H-1,4,8a-triaza-s-indacene and 2-(R)-methyl-pyrrolidine provided the title compound.

MS (ES): [M+1]$^+$ calc'd $C_{23}H_{28}ClN_4O$, 411; found: 411.

The following compounds were prepared according to the procedures described in Scheme 2.

| Structure | Chemical Name | [M + 1]$^+$ Calculated | [M + 1]$^+$ Found |
|---|---|---|---|
| 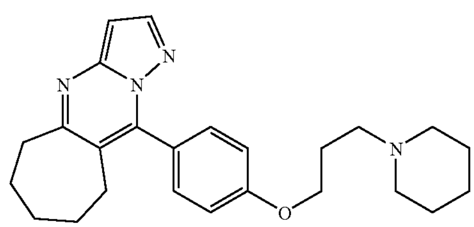 | 10-[4-(3-Piperidin-1-yl-propoxy)-phenyl]-6,7,8,9-tetrahydro-5H-1,4,10a-triaza-cyclohepta[f]indene | 405 | 405 |
| 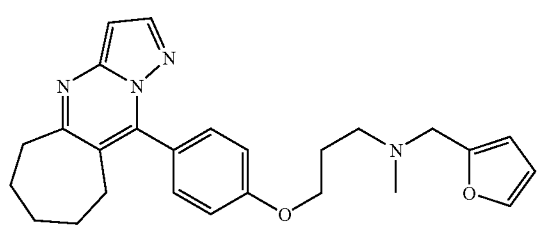 | Furan-2-ylmethyl methyl-{3-[4-(6,7,8,9-tetrahydro-5H-1,4,10a-triaza-cyclohepta[f]inden-10-yl)-phenoxy]-propyl}-amine | 431 | 431 |
| 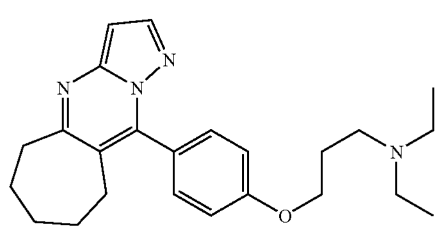 | Diethyl-{3-[4-(6,7,8,9-tetrahydro-5H-1,4,10a-triaza-cyclohepta[f]inden-10-yl)-phenoxy]-propyl}-amine | 393 | 393 |

-continued

| Structure | Chemical Name | [M + 1]+ Calculated | [M + 1]+ Found |
|---|---|---|---|
| 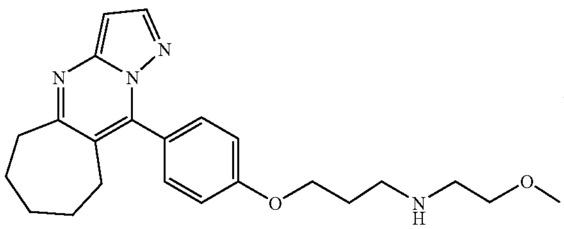 | (2-Methoxy-ethyl)-{3-[4-(6,7,8,9-tetrahydro-5H-1,4,10a-triaza-cyclohepta[f]inden-10-yl)-phenoxy]-propyl}-amine | 395 | 395 |
| 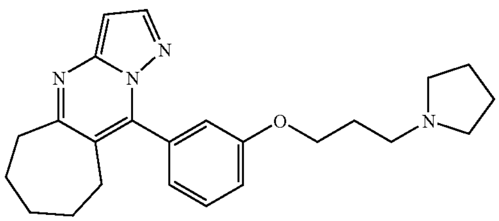 | 10-[3-(3-Pyrrolidin-1-yl-propoxy)-phenyl]-6,7,8,9-tetrahydro-5H-1,4,10a-triaza-cyclohepta[f]indene | 391 | 391 |
| 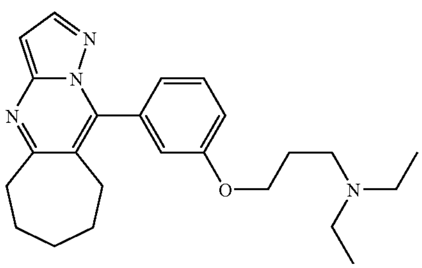 | Diethyl-{3-[3-(6,7,8,9-tetrahydro-5H-1,4,10a-triaza-cyclohepta[f]inden-10-yl)-phenoxy]-propyl}-amine | 393 | 393 |
| 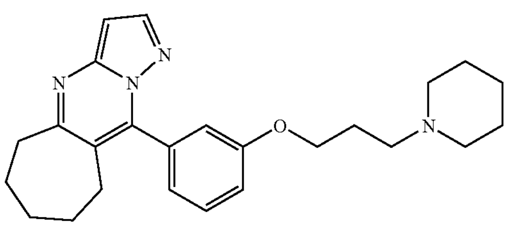 | 10-[3-(3-Piperidin-1-yl-propoxy)-phenyl]-6,7,8,9-tetrahydro-5H-1,4,10a-triaza-cyclohepta[f]indene | 405 | 405 |
| 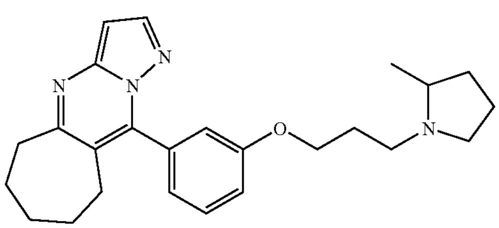 | 10-[3-(3-Methyl-pyrrolidin-1-yl)-propoxy]-phenyl}-6,7,8,9-tetrahydro-5H-1,4,10a-triaza-cyclohepta[f]indene | 405 | 405 |
| 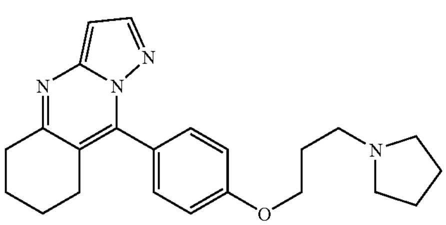 | 9-[4-(3-Pyrrolidin-1-yl-propoxy)-phenyl]-5,6,7,8-tetrahydro-pyrazolo[5,1-b]quinazoline | 377 | 377 |

| Structure | Chemical Name | [M + 1]+ Calculated | [M + 1]+ Found |
|---|---|---|---|
| 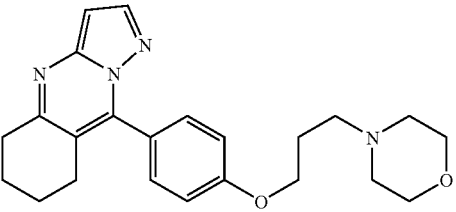 | 9-[4-(3-Morpholin-4-yl-propoxy)-phenyl]-5,6,7,8-tetrahydro-pyrazolo[5,1-b]quinazoline | 394 | 394 |
| 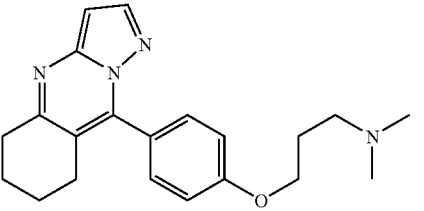 | Dimethyl-{3-[4-(5,6,7,8-tetrahydro-pyrazolo[5,1-b]quinazolin-9-yl)-phenoxy]-propyl}-amine | 351 | 351 |
| 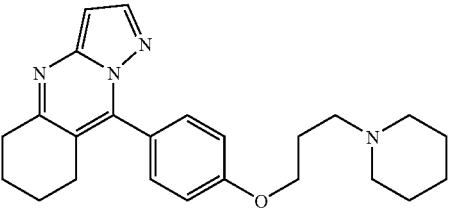 | 9-[4-(3-Piperidin-1-yl-propoxy)-phenyl]-5,6,7,8-tetrahydro-pyrazolo[5,1-b]quinazoline | 391 | 391 |
| 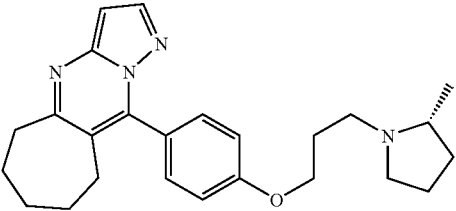 | 10-{4-[3-(2-(R)-Methyl-pyrrolidin-1-yl)-propoxy]-phenyl}-6,7,8,9-tetrahydro-5H-1,4,10a-triaza-cyclohepta[f]indene | 405 | 405 |
| 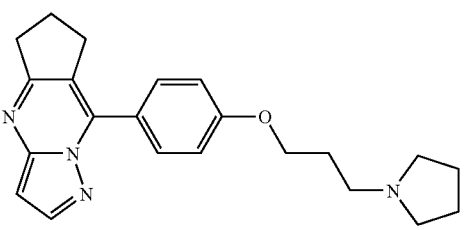 | 8-[4-(3-Pyrrolidin-1-yl-propoxy)-phenyl]-6,7-dihydro-5H-1,4,8a-triaza-s-indacene | 363 | 363 |
| 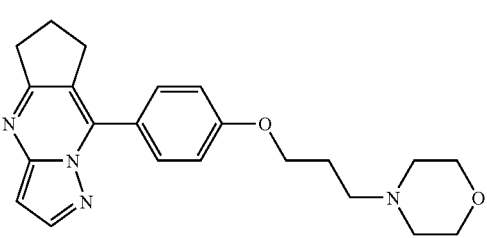 | 8-[4-(3-Morpholin-4-yl-propoxy)-phenyl] 6,7-dihydro-5H-1,4,8a-triaza-s-indacene | 379 | 379 |

-continued
| Structure | Chemical Name | [M + 1]+ Calculated | [M + 1]+ Found |
|---|---|---|---|
| 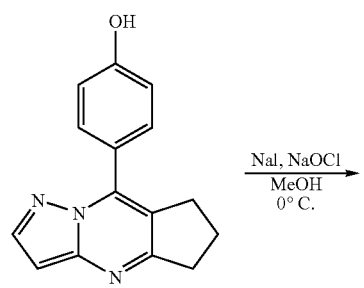 | {3-[4-(6,7-Dihydro-5H-1,4,8a-triaza-s-indacen-8-yl)-phenoxy]-propyl}-dimethyl-amine | 337 | 337 |
| 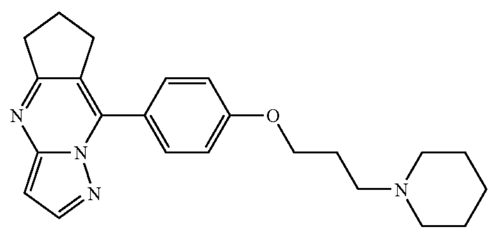 | 8-[4-(3-Piperidin-1-yl-propoxy)-phenyl]-6,7-dihydro-5H-1,4,8a-triaza-2-indacene | 377 | 377 |
| 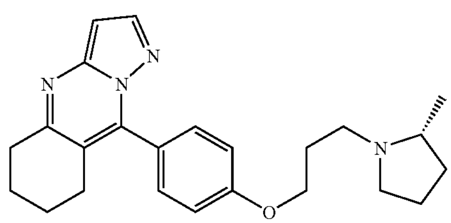 | 9-{4-[3-(2-(R)-Methyl-pyrrolidin-1-yl)-propoxy]-phenyl}-5,6,7,8-tetrahydro-pyrazolo[5,1-b]quinazoline | 391 | 391 |
Scheme 3
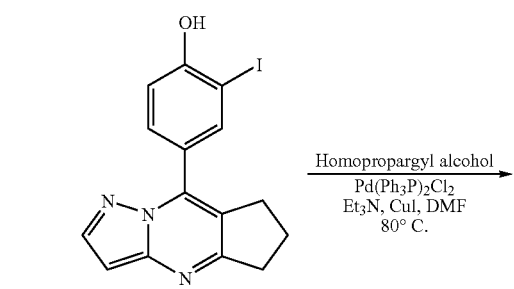
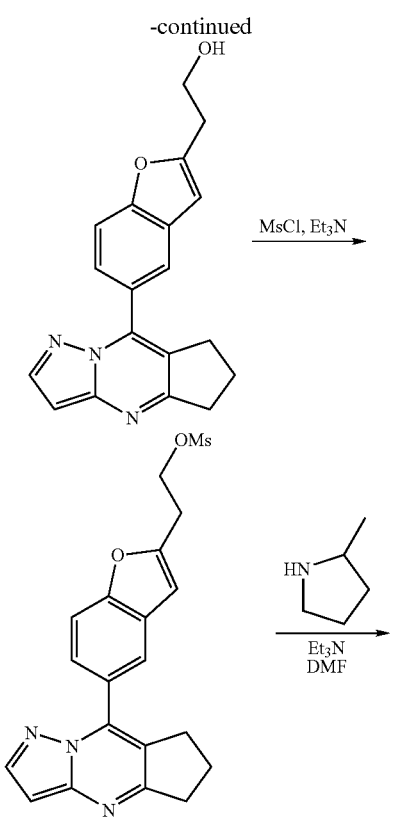

-continued

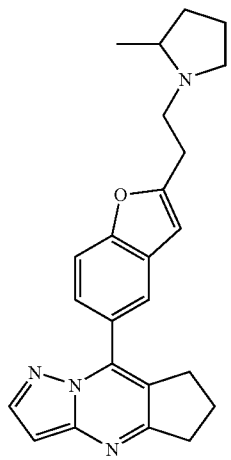

EXAMPLE 8

4-(6,7-Dihydro-5H-1,4,8a-triaza-s-indacen-8-yl)-2-iodo-phenol 4-(6,7-Dihydro-5H-1,4,8a-triaza-s-indacen-8-yl)-phenol (500 mg, 0.002 mmol) was dissolved in methanol (10 mL) followed by addition of NaI (368 mg, 2.45 mmol) and NaOH (98 mg, 2.45 mmol). The solution was cooled to 0° C. followed by dropwise addition of NaOCl (5.25% aq, 3.8 ml) over 3 minutes. The reaction mixture was stirred at 0° C. for 1 hour followed by warming to room temperature and quenching with sodium thiosulphate (saturated. aq., 6 ml). The pH of the reaction was adjusted to ~7 by addition of sodium dihydrogen phosphate. The solution was extracted with $CH_2Cl_2$. The organic layer was dried and concentrated. The residue was purified on silica gel (10%→60% EtOAc in hexane) to give 4-(6,7-dihydro-5H-1,4,8a-triaza-s-indacen-8-yl)-2-iodo-phenol.

LC-Mass (ES): $[M+1]^+$ calc'd for $C_{15}H_{13}IN_3O$, 378; found, 378.

2-[5-(6,7-Dihydro-5H-1,4,8a-triaza-s-indacen-8-yl)-benzofuran-2-yl]-ethanol 4-(6,7-Dihydro-5H-1,4,8a-triaza-s-indacen-8-yl)-2-iodo-phenol (440 mg, 1.17 mmol), homopropargyl alcohol (147.3 mg, 2.1 mmol) and triethyl amine (295 mg, 2.92 mmol) were dissolved in DMF (15 ml). To this solution was added copper (I) iodide (66.3 mg, 0.34 mmol) and bis-triphenylphosphine palladium (II) chloride (81.9 mg, 0.117 mmol). The reaction was flushed with nitrogen and heated at 65° C. for 12 hours. Solvent was removed under reduced pressure and the residue purified on silica gel (10%-75% EtOAc in hexane) to give 2-[5-(6,7-dihydro-5H-1,4,8a-triaza-s-indacen-8-yl)-benzofuran-2-yl]-ethanol.

$[M+1]^+$ calc'd for $C_{19}H_{18}N_3O_2$, 320; found, 320.

Methanesulfonic acid 2-[5-(6,7-dihydro-5H-1,4,8a-triaza-s-indacen-8-yl)-benzo-furan-2-yl]-ethyl ester To a room temperature solution of 2-[5-(6,7-Dihydro-5H-1,4,8a-triaza-s-indacen-8-yl)-benzofuran-2-yl]-ethanol (200 mg, 0.91 mmol) in $CH_2Cl_2$ (10 ml) was added triethylamine (303 mg, 3 mmol) and methanesulfonyl chloride (525 mg, 4.56 mmol). The mixture was stirred at room temperature for 30 minutes. Water was added to the reaction and the organic layer separated. The aqueous layer was extracted with $CH_2Cl_2$ and the combined organic extracts were dried and concentrated to give methanesulfonic acid 2-[5-(6,7-dihydro-5H-1,4,8a-triaza-s-indacen-8-yl)-benzo-furan-2-yl]-ethyl ester, which was used in the next reaction without further purification.

$[M+1]^+$ calcd for $C_{20}H_{20}N_3O_4S$, 398; found, 398.

8-{2-[2-(2-Methyl-pyrrolidin-1-yl)-ethyl]-benzofuran-5-yl}-6,7-dihydro-5H-1,4,8a-triaza-s-indacene Methanesulfonic acid 2-[5-(6,7-dihydro-5H-1,4,8a-triaza-s-indacen-8-yl)-benzo-furan-2-yl]-ethyl ester (0.085 mmol) was dissolved in acetonitrile (2 ml) followed by addition of 2-methylpyrrolidine (0.85 mmol) and potassium carbonate (0.425 mmol) and heated to 70° C. for 24 hours. The reaction was cooled, filtered and concentrated. The residue was purified via preparative HPLC to give the title compound.

$[M+1]^+$ calc'd for $C_{24}H_{27}N_4O$, 387; found, 387.

EXAMPLE 9

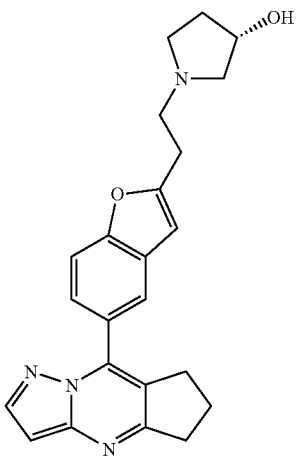

1-{2-[5-(6,7-Dihydro-5H-1,4,8a-triaza-s-indacen-8-yl)-benzofuran-2-yl]-ethyl}-pyrrolidin-3-(S)-ol Methanesulfonic acid 2-[5-(6,7-dihydro-5H-1,4,8a-triaza-s-indacen-8-yl)-benzo-furan-2-yl]-ethyl ester (0.085 mmol) described above was dissolved in acetonitrile (2 ml) followed by addition of 3-(S)-hydroxypyrrolidine (0.85 mmol) and potassium carbonate (0.425 mmol) and heated to 70° C. for 24 hours. The reaction was cooled, filtered and concentrated. The residue was purified via preparative HPLC to give 1-{2-[5-(6,7-Dihydro-5H-1,4,8a-triaza-s-indacen-8-yl)-benzofuran-2-yl]-ethyl}-pyrrolidin-3-(S)-ol.

$[M+1]^+$ calc'd for $C_{23}H_{25}N_4O_2$, 389; found, 389.

EXAMPLE 10

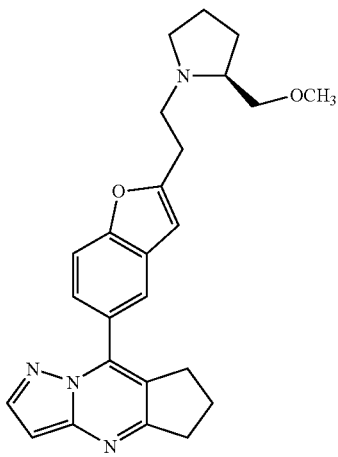

8-12-[2-(2-(S)-Methoxymethyl-pyrrolidin-1-yl)-ethyl]-benzofuran-5-yl)-6,7-dihydro-5H-1,4,8a-triaza-s-indacene Methanesulfonic acid 2-[5-(6,7-dihydro-5H-1,4,8a-triaza-s-indacen-8-yl)-benzo-furan-2-yl]-ethyl ester (0.085 mmol) described above was dissolved in acetonitrile (2 ml) followed by addition of 2-(S)-methoxymethylpyrrolidine (0.85 mmol) and potassium carbonate (0.425 mmol) and heated to 70° C. for 24 hours. The reaction was cooled, filtered and concentrated. The residue was purified via preparative HPLC to give the title compound.

$[M+1]^+$ calc'd for $C_{25}H_{29}N_4O_2$, 417; found, 417.

EXAMPLE 11

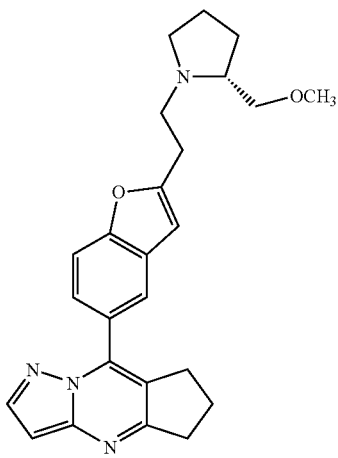

8-{2-[2-(2-(R)-Methoxymethyl-pyrrolidin-1-yl)-ethyl]-benzofuran-5-yl}-6,7-dihydro-5H-1,4,8a-triaza-s-indacene Methanesulfonic acid 2-[5-(6,7-dihydro-5H-1,4,8a-triaza-s-indacen-8-yl)-benzo-furan-2-yl]-ethyl ester (0.085 mmol) described above was dissolved in acetonitrile (2 ml) followed by addition of 2-(R)-methoxymethylpyrrolidine (0.85 mmol) and potassium carbonate (0.425 mmol) and heated to 70° C. for 24 hours. The reaction was cooled, filtered and concentrated. The residue was purified via preparative HPLC to give the desired 8-{2-[2-(2-(R)-Methoxymethyl-pyrrol idin-1-yl)-ethyl]-benzofuran-5-yl}-6,7-dihydro-5H-1,4,8a-triaza-s-indacene.

$[M+1]^+$ calc'd for $C_{25}H_{29}N_4O_2$, 417; found, 417.

EXAMPLE 12

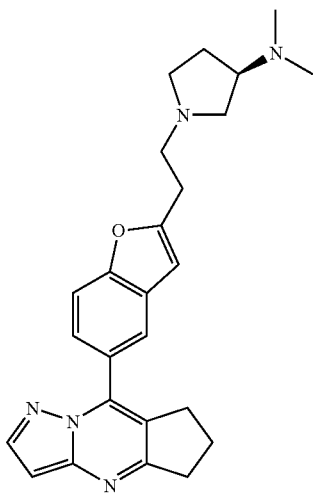

8-{2-[2-(3-(R)-Dimethylamino-pyrrolidin-1-yl)-ethyl]-benzofuran-5-yl}-6,7-dihydro-5H-1,4,8a-triaza-s-indacene Methanesulfonic acid 2-[5-(6,7-dihydro-5H-1,4,8a-triaza-s-indacen-8-yl)-benzo-furan-2-yl]-ethyl ester (0.085 mmol) described above was dissolved in acetonitrile (2 ml) followed by addition of 3-(R)-dimethylaminopyrrolidine (0.85 mmol) and potassium carbonate (0.425 mmol) and heated to 70° C. for 24 hours. The reaction was cooled, filtered and concentrated. The residue was purified via preparative HPLC to give 8-{2-[2-(3-(R)-Dimethylamino-pyrrolidin-1-yl)-ethyl]-benzofuran-5-yl}-6,7-dihydro-5H-1,4,8a-triaza-s-indacene.

$[M+1]^+$ calc'd for $C_{25}H_{30}N_5O$, 416; found, 416.

The following compounds were prepared according to the procedures described in Scheme 3.

| Structure | Chemical Name | [M + 1]+ Calculated | [M + 1]+ Found |
|---|---|---|---|
| 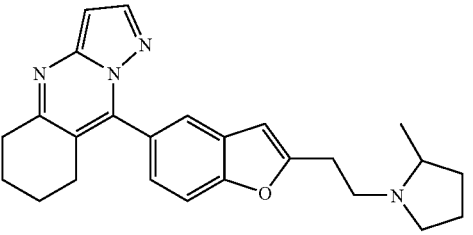 | 9-{2-[2-(2-Methyl-pyrrolidin-1-yl)-ethyl]-benzofuran-5-yl}-5,6,7,8-tetrahydro-pyrazolo[5,1-b]quinazoline | 387 | 387 |
| 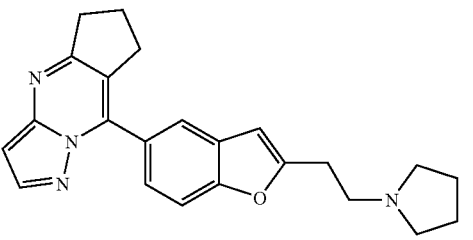 | 8-[2-(2-Pyrrolidin-1-yl-ethyl)-benzofuran-5-yl]-6,7-dihydro-5H-1,4,8a-triaza-s-indacene | 373 | 373 |
| 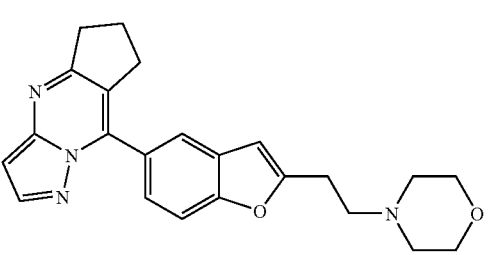 | 8-[2-(2-Morpholin-4-yl-ethyl)-benzofuran-5-yl]-6,7-dihydro-5H-1,4,8a-triaza-s-indacene | 389 | 389 |
| 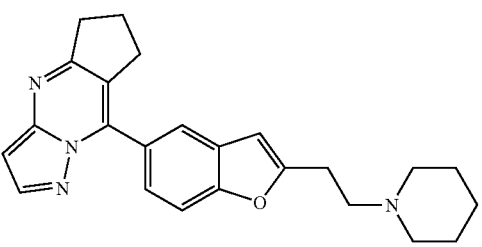 | 8-[2-(2-Piperidin-1-yl-ethyl)-benzofuran-5-yl]-6,7-dihydro-5H-1,4,8a-triaza-s-indacene | 387 | 387 |
| 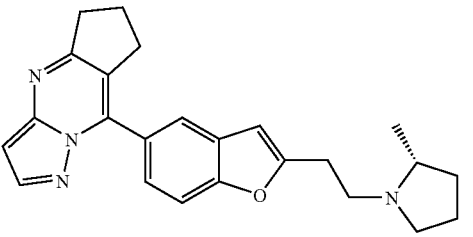 | 8-{2-[2-(2-(R)-Methyl-pyrrolidin-1-yl)-ethyl]-benzofuran-5-yl}-6,7-dihydro-5H-1,4,8a-triaza-s-indacene | 387 | 387 |
| 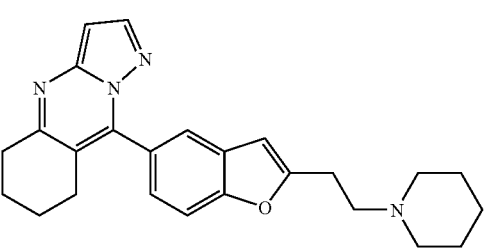 | 9-[2-(2-Piperidin-1-yl-ethyl)-benzofuran-5-yl]-5,6,7,8-tetrahydro-pyrazolo[5,1-b]quinazoline | 401 | 401 |

| Structure | Chemical Name | [M + 1]+ Calculated | [M + 1]+ Found |
|---|---|---|---|
| 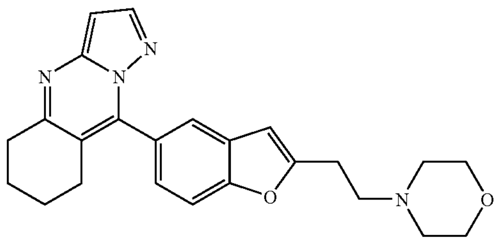 | 9-[2-(2-Morpholin-4-yl-ethyl)-benzofuran-5-yl]-5,6,7,8-tetrahydro-pyrazolo[5,1-b]quinazoline | 403 | 403 |
| 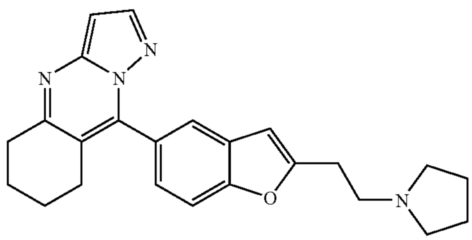 | 9-[2-(2-Pyrrolidin-1-yl-ethyl)-benzofuran-5-yl]-5,6,7,8-tetrahydro-pyrazolo[5,1-b]quinazoline | 387 | 387 |
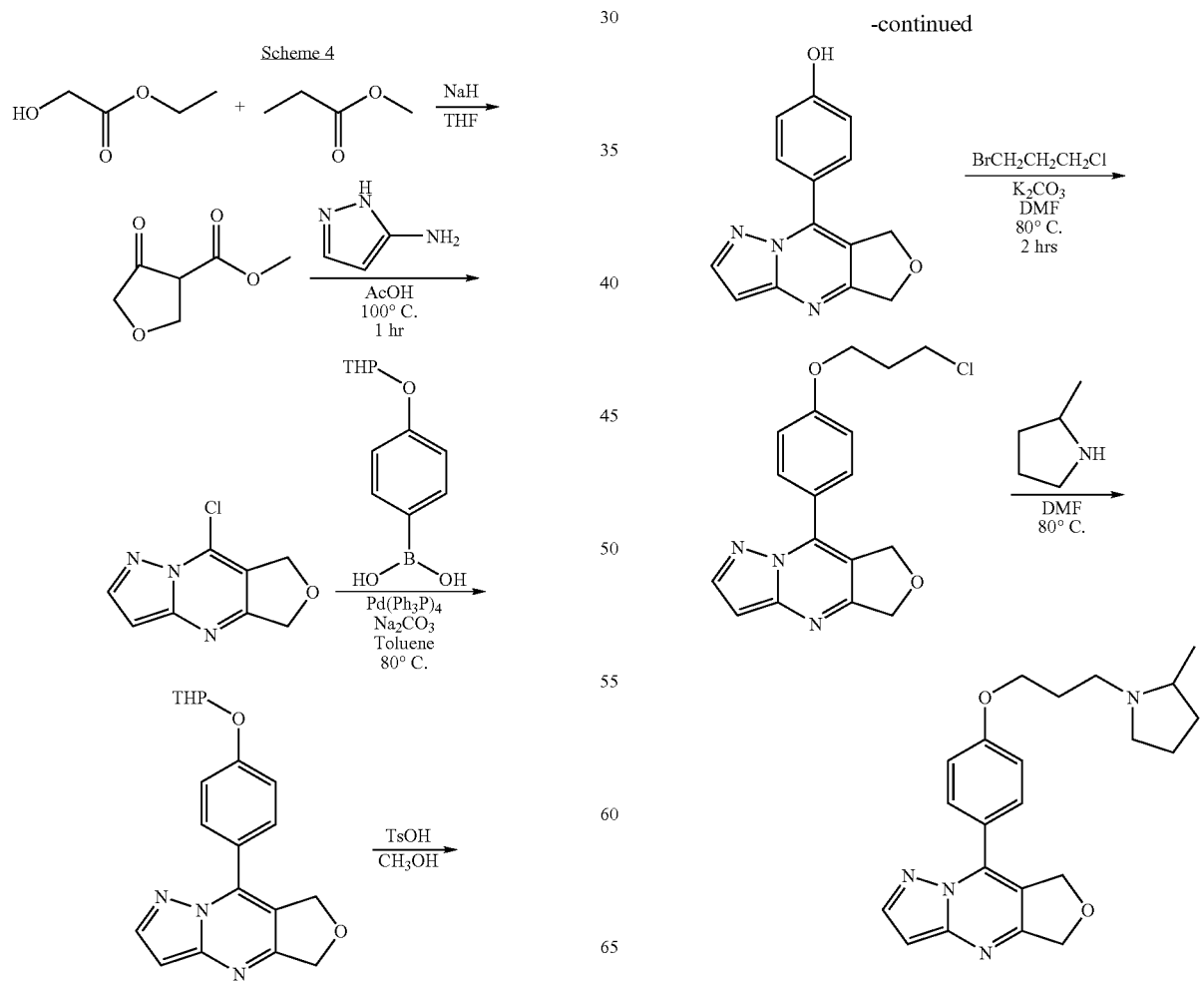

EXAMPLE 13

4-Oxo-tetrahydro-furan-3-carboxylic acid methyl ester

To a stirred slurry of sodium hydride (1.67 g, 60% in mineral oil, 44.0 mmol) in dried ether was added with ethyl glycolate, dropwise over 15 minutes. The reaction was warmed up to room temperature for 30 min while stirring and concentrated in vacuo to provide white solid. The solid was treated with methyl acrylate (4.16 g, 49 mmol) in DMSO (20 mL) at 0° C. for 15 minutes and room temperature for 45 minutes. The mixture was poured into 5% $H_2SO_4$ and extracted with ethyl acetate. Organic layer was washed with brine, dried over $Mg_2SO_4$ and concentrated to give 4-oxo-tetrahydro-furan-3-carboxylic acid methyl ester as a colorless oil.

MS (ES): $[M-1]^-$ cal'cd for $C_6H_7O_3$, 143; found: 143.

5H,7H-6-Oxa-1,4,8a-triaza-s-indacen-8-ol

Using the method described for the preparation of 6,7,8,9-Tetrahydro-5H-1,4,10a-triaza-cyclohepta[f]inden-10-ol, the reaction of 4-oxo-tetrahydro-furan-3-carboxylic acid methyl ester and 2H-pyrazol-3-ylamine in acetic acid provided the desired 5H,7H-6-Oxa-1,4,8a-triaza-s-indacen-8-ol.

MS (ES): $[M+1]^+$ calc'd for $C_8H_8N_3O_2$, 178; found: 178.

8-Chloro-5H,7H-6-oxa-1,4,8a-triaza-s-indacene

Using the method described for the preparation of 10-chloro-6,7,8,9-tetrahydro-5H-1,4,10a-triaza-cyclohepta[f]indene, the reaction of 5H,7H-6-Oxa-1,4,8a-triaza-s-indacen-8-ol and phosphorus oxychloride provided the title compound.

MS (ES): $[M+1]^+$ calc'd for $C_8H_6ClN_3O$, 196; found: 196.

8-[4-(Tetrahydro-pyran-2-yloxy)-phenyl]-5H,7H-6-oxa-1,4,8a-triaza-s-indacene Using the method described for the preparation of 10-(4-benzyloxy-phenyl)-6,7,8,9-tetrahydro-5H-1,4,10a-triaza-cyclohepta[f]indene, the reaction of 8-Chloro-5H,7H-6-oxa-1,4,8a-triaza-s-indacene and 4-(Tetrahydro-pyran-2-yloxy)-phenyl boronic acid provided the title compound.

MS (ES): $[M+1]^+$ calc'd for $C_{19}H_{20}N_3O_3$, 338; found: 338.

4-(5,6,7,8-Tetrahydro-pyrazolo[5,1-b]quinazolin-9-yl)-phenol

8-[4-(Tetrahydro-pyran-2-yloxy)-phenyl]-5H,7H-6-oxa-1,4,8a-triaza-s-indacene (500 mg, 2.5 mmol) was suspended in methanol and added with p-toluenesulfonic acid (50 mg) was catalyst. The mixture was stirred at room temperature for 2 hours and concentrated in vacuo. The residue was carried on to the next reaction without purification.

8-[4-(3-Chloro-propoxy)-phenyl]-5H,7H-6-oxa-1,4,8a-triaza-s-indacene

Using the method described for the preparation of 10-[4-(3-Chloro-propoxy)-phenyl]-6,7,8,9-tetrahydro-5H-1,4,10a-triaza-cyclohepta[f]indene, the reaction of 4-(5,6,7,8-tetrahydro-pyrazolo[5,1-b]quinazolin-9-yl)-phenol and 1-bromo-3-chloropropane provided the title compound which was used without further purification.

8-{4-[3-(2-Methyl-pyrrolidin-1-yl)-propoxy]-phenyl}-5H,7H-6-oxa-1,4,8a-triaza-s-indacene Using the method described for the preparation of 10-{4-[3-(2-Methyl-pyrrolidin-1-yl)-propoxy]-phenyl}-6,7,8,9-tetrahydro-5H-1,4,10a-triaza-cyclohepta[t]indene, the reaction of 8-[4-(3-Chloro-propoxy)-phenyl]-5H,7H-6-oxa-1,4,8a-triaza-s-indacene and 2-methyl-pyrrolidine provided compound.

MS (ES): $[M+1]^+$ calcd $C_{22}H_{27}N_4O_2$, 379; found: 379.

Representative compounds of the present invention that were prepared by the procedures of the Examples were evaluated in binding assays against cells expressing the mouse and human $H_3$ receptor by the following procedure.

Cell Culture

An HT1080 cell line was produced that expresses the human $H_3$ receptor. Expression of this receptor was provided by utilization of the RAGE methodology (Harrington et al., 2001) Nature Biotechol. 19:440-5. This cell line was transfected with the chimeric G-protein Gqαi5 (Conklin et al., 1993) Nature 363:274-6 to facilitate assessment of receptor activation through the analysis of intercellular $Ca^{++}$ levels using a fluorescence assay. The HT1080 cells expressing human histamine $H_3$ receptor and Gqαi5 were grown in alpha-modified MEM containing 10% FBS, 3 ug/ml puromycin, 7 ug/ml blasticidin, and 3.2 uM methotrexate at 37° C. in 5% CO2/95% atmosphere.

Membrane Preparation

Cells were washed with cold PBS buffer twice, scraped off the plates, and centrifuged at 1000×g for 5 minutes. Cells were resuspended in ice-cold buffer of 10 mM Tris, pH 7.4, 5 mM EDTA, protease inhibitor cocktail tablets (Roche Molecular Biochemicals) and incubated on ice for 10 minutes. The mixture was then homogenized with a dounce homogenizer or a polytron tissue grinder and centrifuged at 1000×g for 10 min at 4° C. The supernatant was centrifuged at 32,000×g for 30 min at 4° C. The membrane pellet was resuspended in a buffer of 50 mM Tris, pH 7.4 with protease inhibitor cocktail tablets and stored at −80° C. until use. Protein concentration was determined by the methods of Bradford.

Radioligand Binding Assays

Membranes were homogenized in buffer containing 50 mM Tris/HCl, 1 mM EDTA pH 7.4, and protease inhibitor cocktail tablets. Dissociation constants of radioligand ($K_D$ values) and maximum binding sites ($B_{max}$) were determined in saturation binding experiments. $K_i$ and $IC_{50}$ were determined in competition binding assays using a fixed amount of radioligand.

Saturation binding assays were carried out in 96-well polypropylene plates in triplicate or quadruplicate. Reaction mixtures contained 100 µl of membrane suspension (~100 µg/well), 50 µl of 4% DMSO, 50 µl of increasing amounts of [$^3$H]N$^\alpha$-methylhistamine (final concentration of 0.01-20 nM). Nonspecific binding was defined with 10 uM clobenpropit. Competition binding assays were performed in a reaction mixture containing 100 µl of membrane suspension, 50 µl of [H]N$^\alpha$-methylhistamine (final concentration of ~2 nM), and 50 µl compounds. Compounds were dissolved in DMSO to 10 mM and then diluted with 4% DMSO; the final DMSO concentrations did not exceed 1%. Incubations were carried out for 1.5 hours at room temperature. Reactions were terminated by rapid filtration over glass fibre GF/C filters (Perkin Elmers, MA) that had been presoaked in 0.3% PEI, using a Brandel cell harvester. The filters were washed with 500 ml of ice-cold buffer containing 50 mM Tris-HCl, pH 7.4, and were subsequently dried, impregnated with Meltilex wax scintillate (Perkin Elmers, MA) and counted with a Betaplate scintillation counter (Perkin Elmers, MA).

Calcium Mobilization

NT1050 cells expressing human $H_3$ receptor ($10^4$/well) were seeded in black 384-well plates and incubated overnight at 37° C. in a 5% CO2/95% atmosphere. After removing medium, cells were treated with CsCl Ringer's buffer (136 mM CsCl, 5.4 mM KCl, 5.5 mM D-Glucose, 20 mM Hepes, pH 7.5, 2.1 mM $MgCl_2$, 1.2 mM $CaCl_2$) containing the Calcium3 dye (Molecular Device, CA) and probenecid (3.75 mM) for 60 minutes according to manufacture's instruction. Compounds were diluted in CsCl Ringer's buffer containing 0.2% bovine serum albumin and 1.0% DMSO. The concentration of R-α-methylhistamine required to stimulate 75% of maximum response was used to test compounds. Ligand-induced fluorescence was measured on a Fluorometric Imaging Plate Reader (FLIPR, Molecular Device, CA).

Data Analysis

All data were analyzed by nonlinear least square curve fitting using Prism 4.0 software. The $K_D$ for [$^3$H]N$^\alpha$-methylhistamine and the $B_{max}$ were derived from equation $RL=R_fL/(K_D+L)$. RL is concentration of receptor-bound ligand at equilibrium, L is the free ligand concentration, $R_f$ is the total receptor concentration. For competition binding experiments, $IC_{50}$ (the concentration of compound producing 50% inhibition of specific binding) was derived from fitting to a 4-parameter logistic equation. Apparent Ki values were calculated using the Cheng-Prussof equation of $Ki=IC_{50}/(1+(L)/Kd)$, L is the ligand concentration. Agonist stimulation and antagonist inhibition in FLIPR were fitted to sigmoidal dose response using equation Y=Bottom+(Top-Bottom)/(1+10^((LogEC50-X))), X is the logarithm of concentration of compounds. Y is the response.

| Structure | Chemical Name | Mouse H3 (µM) | Human H3 (µM) |
|---|---|---|---|
| 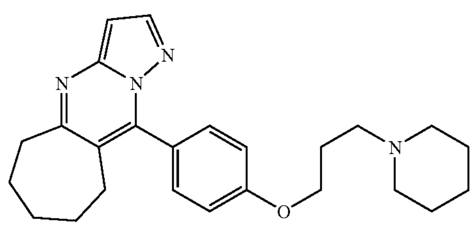 | 10-[4-(3-Piperidin-1-yl-propoxy)-phenyl]-6,7,8,9-tetrahydro-5H-1,4,10a-triaza-cyclohepta[f]indene | <0.05 | <0.05 |
| 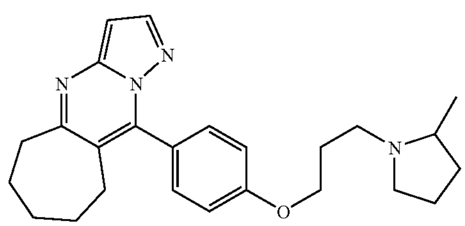 | 10-{4-[3-(2-Methyl-pyrrolidin-1-yl)-propoxy]-phenyl}-6,7,8,9-tetrahydro-5H-1,4,10a-triaza-cyclohepta[f]indene | <0.05 | <0.05 |
| 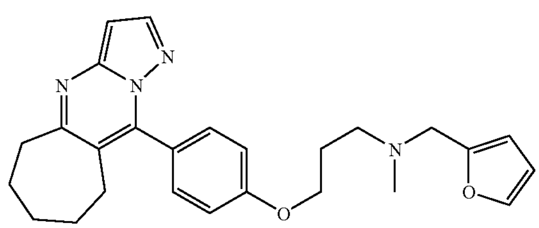 | Furan-2-ylmethyl-methyl-{3-[4-(6,7,8,9-tetrahydro-5H-1,4,10a-triaza-cyclohepta[f]inden-10-yl)-phenoxy]-propyl}-amine | <0.5 | <5 |
| 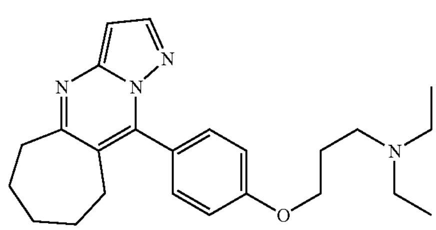 | Diethyl-{3-[4-(6,7,8,9-tetrahydro-5H-1,4,10a-triaza-cyclohepta[f]inden-10-yl)-phenoxy]-propyl}-amine | <0.5 | <0.05 |

-continued

| Structure | Chemical Name | Mouse H3 (μM) | Human H3 (μM) |
|---|---|---|---|
| 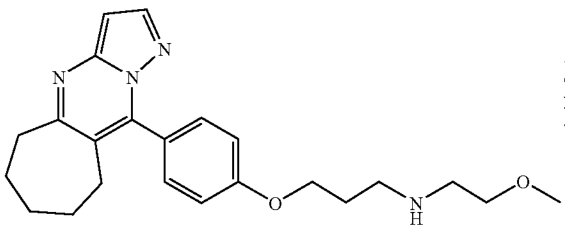 | (2-Methoxy-ethyl)-{3-[4-(6,7,8,9-tetrahydro-5H-1,4,10a-triaza-cyclohepta[f]inden-10-yl)-phenoxy]-propyl}-amine | <5 | nd |
| 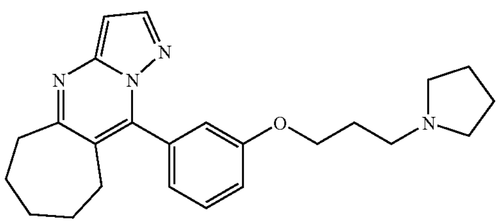 | 10-[3-(3-Pyrrolidin-1-yl-propoxy)-phenyl]-6,7,8,9-tetrahydro-5H-1,4,10a-triaza-cyclohepta[f]indene | <5 | <0.5 |
| 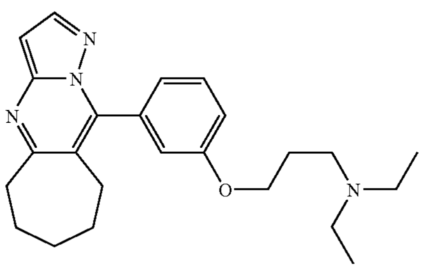 | Diethyl-{3-[3-(6,7,8,9-tetrahydro-5H-1,4,10a-triaza-cyclohepta[f]inden-10-yl)-phenoxy]-propyl}-amine | <5 | |
| 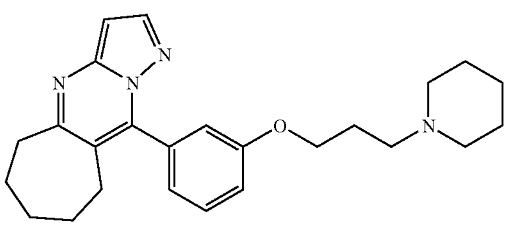 | 10-[3-(3-Piperidin-1-yl-propoxy)-phenyl]-6,7,8,9-tetrahydro-5H-1,4,10a-triaza-cyclohepta[f]indene | <5 | <0.5 |
| 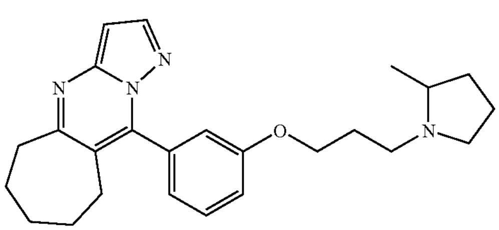 | 10-{3-[3-(2-Methyl-pyrrolidin-1-yl)-propoxy]-phenyl}-6,7,8,9-tetrahydro-5H-1,4,10a-triaza-cyclohepta[f]indene | <5 | |
| 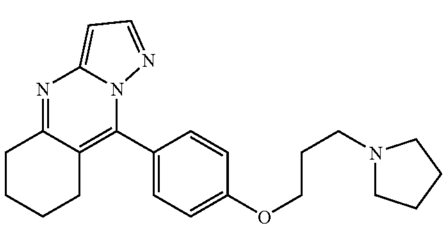 | 9-[4-(3-Pyrrolidin-1-yl-propoxy)-phenyl]-5,6,7,8-tetrahydro-pyrazolo[5,1-b]quinazoline | <0.05 | <0.05 |

-continued

| Structure | Chemical Name | Mouse H3 (μM) | Human H3 (μM) |
|---|---|---|---|
| 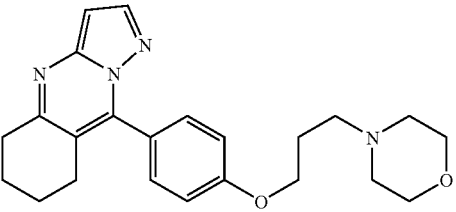 | 9-[4-(3-Morpholin-4-yl-propoxy)-phenyl]-5,6,7,8-tetrahydro-pyrazolo[5,1-b]quinazoline | <0.05 | <0.05 |
| 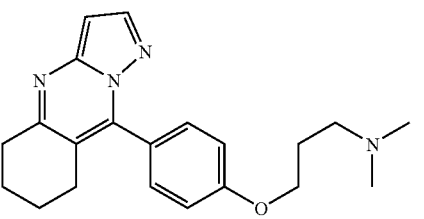 | Dimethyl-{3-[4-(5,6,7,8-tetrahydro-pyrazolo[5,1-b]quinazolin-9-yl)-phenoxy]-propyl}-amine | <0.5 | <0.05 |
| 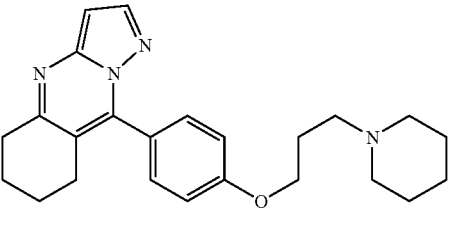 | 9-[4-(3-Piperidin-1-yl-propoxy)-phenyl]-5,6,7,8-tetrahydro-pyrazolo[5,1-b]quinazoline | <0.05 | <0.05 |
| 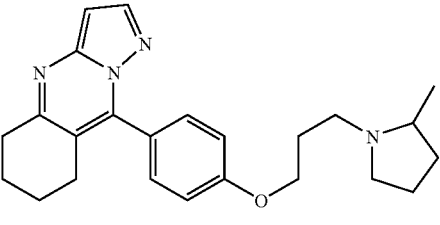 | 9-{4-[3-(2-Methyl-pyrrolidin-1-yl)-propoxy]-phenyl}-5,6,7,8-tetrahydro-pyrazolo[5,1-b]quinazoline | <0.05 | <0.05 |
| 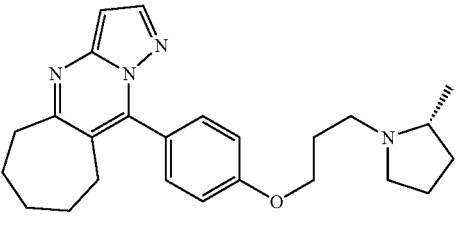 | 10-{4-[3-(2-(R)-Methyl-pyrrolidin-1-yl)-propoxy]-phenyl}-6,7,8,9-tetrahydro-5H-1,4,10a-triaza-cyclohepta[f]indene | <0.05 | <0.05 |
| 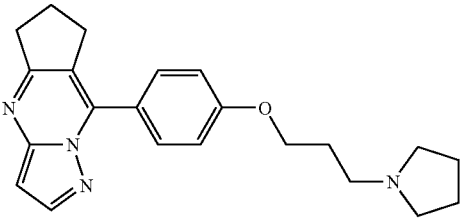 | 8-[4-(3-Pyrrolidin-1-yl-propoxy)-phenyl]-6,7-dihydro-5H-1,4,8a-triaza-s-indacene | <0.05 | <0.05 |

| Structure | Chemical Name | Mouse H3 (μM) | Human H3 (μM) |
|---|---|---|---|
| 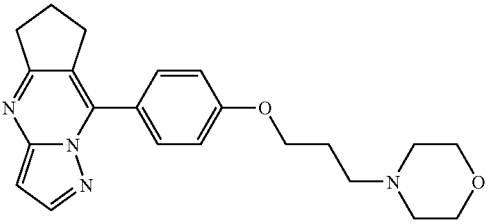 | 8-[4-(3-Morpholin-4-yl-propoxy)-phenyl]-6,7-dihydro-5H-1,4,8a-triaza-s-indacene | <0.5 | <0.05 |
| 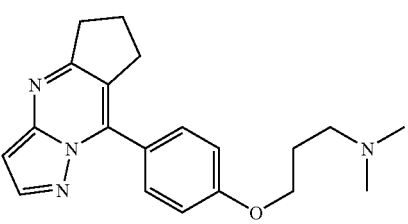 | {3-[4-(6,7-Dihydro-5H-1,4,8a-triaza-s-indacen-8-yl)-phenoxy]-propyl}-dimethyl-amine | <0.5 | <0.05 |
| 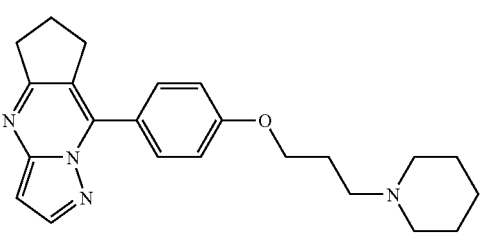 | 8-[4-(3-Piperidin-1-yl-propoxy)-phenyl]-6,7-dihydro-5H-1,4,8a-triaza-s-indacene | <0.05 | <0.05 |
| 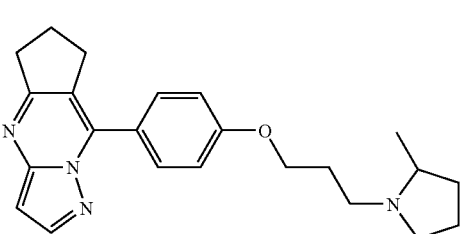 | 8-{4-[3-(2-Methyl-pyrrolidin-1-yl)-propoxy]-phenyl}-6,7-dihydro-5H-1,4,8a-triaza-s-indacene | <0.05 | <0.05 |
| 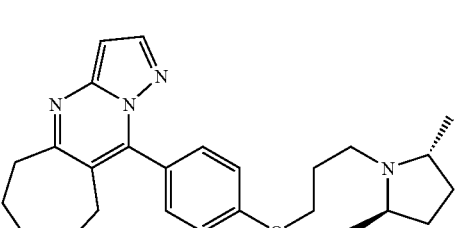 | 10-{4-[3-(2,5-(R,R)-Dimethyl-pyrrolidin-1-yl)-propoxy]-phenyl}-6,7,8,9-tetrahydro-5H-1,4,10a-triaza-cyclohepta[f]indene | <0.5 | <0.05 |
| 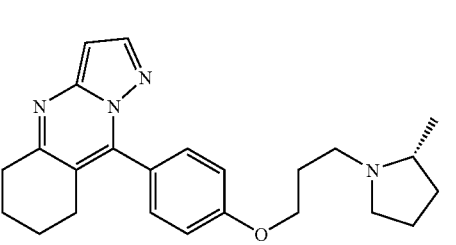 | 9-{4-[3-(2-(R)-Methyl-pyrrolidin-1-yl)-propoxy]-phenyl}-5,6,7,8-tetrahydro-pyrazolo[5,1-b]quinazoline | <0.05 | <0.05 |

| Structure | Chemical Name | Mouse H3 (μM) | Human H3 (μM) |
|---|---|---|---|
| 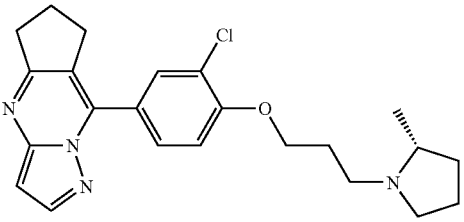 | 8-{3-Chloro-4-[3-(2-(R)-methyl-pyrrolidin-1-yl)-propoxy]-phenyl}-6,7-dihydro-5H-1,4,8a-triaza-s-indacene | <0.05 | <0.05 |
| 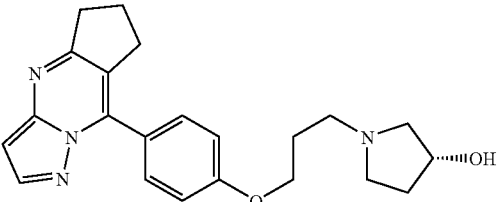 | 1-{3-[4-(6,7-Dihydro-5H-1,4,8a-triaza-s-indacen-8-yl)-phenoxy]-propyl}-pyrrolidin-3-(R)-ol | <0.05 | <0.05 |
| 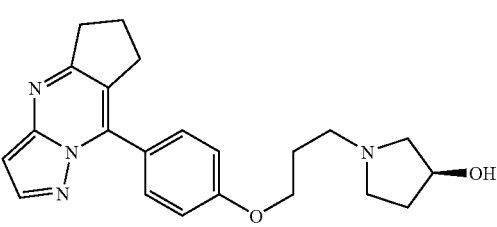 | 1-{3-[4-(6,7-Dihydro-5H-1,4,8a-triaza-s-indacen-8-yl)-phenoxy]-propyl}-pyrrolidin-3-(S)-ol | <0.05 | <0.05 |
| 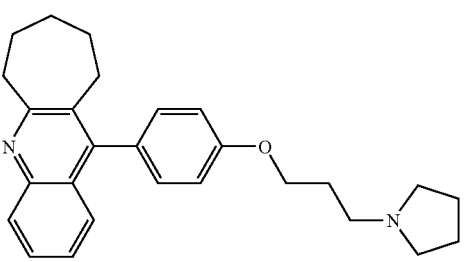 | 11-[4-(3-Pyrrolidin-1-yl-propoxy)-phenyl]-7,8,9,10-tetrahydro-6H-cyclohepta[b]quinoline | <0.5 | <0.05 |
| 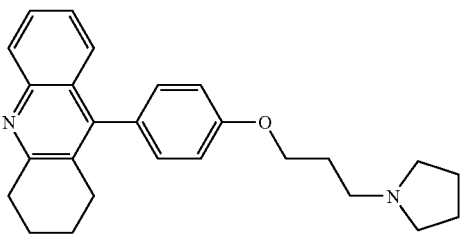 | 9-[4-(3-Pyrrolidin-1-yl-propoxy)-phenyl]-1,2,3,4-tetrahydro-acridine | <0.5 | <0.05 |
| 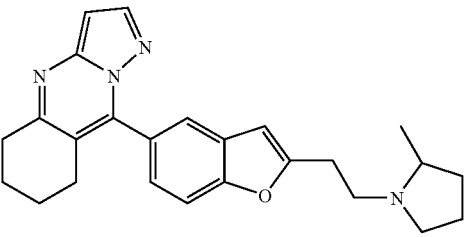 | 9-{2-[2-(2-Methyl-pyrrolidin-1-yl)-ethyl]-benzofuran-5-yl}-5,6,7,8-tetrahydro-pyrazolo[5,1-b]quinazoline | <0.5 | <0.05 |

-continued

| Structure | Chemical Name | Mouse H3 (μM) | Human H3 (μM) |
|---|---|---|---|
| 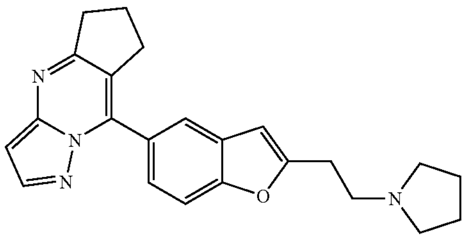 | 8-[2-(2-Pyrrolidin-1-yl-ethyl)-benzofuran-5-yl]-6,7-dihydro-5H-1,4,8a-triaza-s-indacene | <0.5 | <0.05 |
| 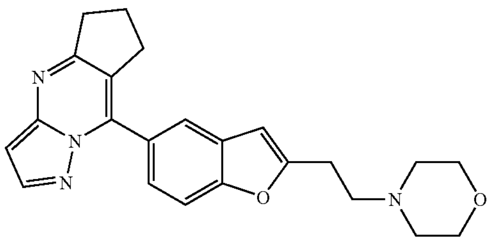 | 8-[2-(2-Morpholin-4-yl-ethyl)-benzofuran-5-yl]-6,7-dihydro-5H-1,4,8a-triaza-s-indacene | <0.5 | <0.05 |
| 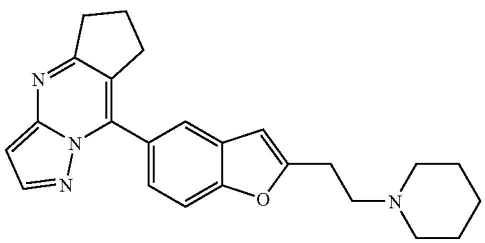 | 8-[2-(2-Piperidin-1-yl-ethyl)-benzofuran-5-yl]-6,7-dihydro-5H-1,4,8a-triaza-s-indacene | <0.5 | <0.05 |
| 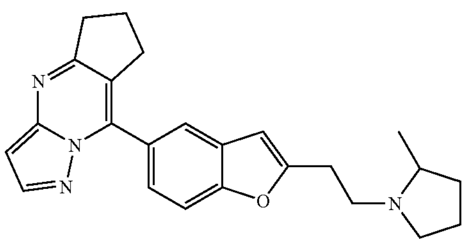 | 8-{2-[2-(2-Methyl-pyrrolidin-1-yl)-ethyl]-benzofuran-5-yl}-6,7-dihydro-5H-1,4,8a-triaza-s-indacene | <0.05 | <0.05 |
| 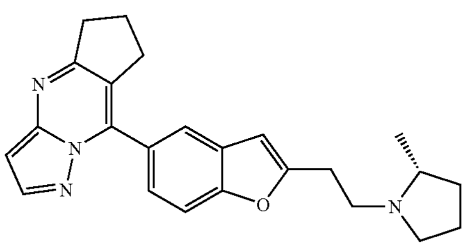 | 8-{2-[2-(2-(R)-Methyl-pyrrolidin-1-yl)-ethyl]-benzofuran-5-yl}-6,7-dihydro-5H-1,4,8a-triaza-s-indacene | <0.05 | <0.05 |
| 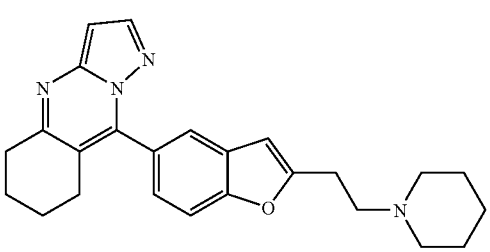 | 9-[2-(2-Piperidin-1-yl-ethyl)-benzofuran-5-yl]-5,6,7,8-tetrahydro-pyrazolo[5,1-b]quinazoline | <5 | <0.05 |

-continued

| Structure | Chemical Name | Mouse H3 (μM) | Human H3 (μM) |
|---|---|---|---|
| 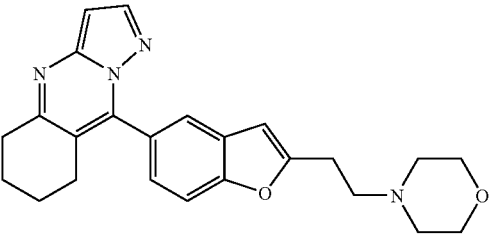 | 9-[2-(2-Morpholin-4-yl-ethyl)-benzofuran-5-yl]-5,6,7,8-tetrahydro-pyrazolo[5,1-b]quinazoline | <0.5 | <0.05 |
| 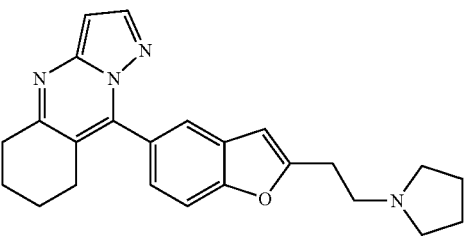 | 9-[2-(2-Pyrrolidin-1-yl-ethyl)-benzofuran-5-yl]-5,6,7,8-tetrahydro-pyrazolo[5,1-b]quinazoline | <5 | <0.5 |
| 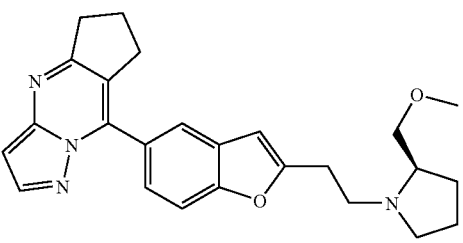 | 8-{2-[2-(R)-(2-Methoxymethyl-pyrrolidin-1-yl)-ethyl]-benzofuran-5-yl}-6,7-dihydro-5H-1,4,8a-triaza-s-indacene | <0.5 | <0.5 |
| 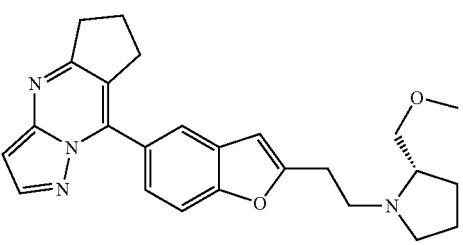 | 8-{2-[2-(2-(S)-Methoxymethyl-pyrrolidin-1-yl)-ethyl]-benzofuran-5-yl}-6,7-dihydro-5H-1,4,8a-triaza-s-indacene | <0.05 | <0.05 |
| 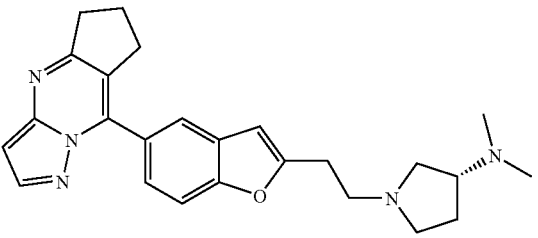 | (1-{2-[5-(6,7-Dihydro-5H-1,4,8a-triaza-s-indacen-8-yl)-benzofuran-2-yl]-ethyl}-pyrrolidin-3-yl)-(R)-dimethyl-amine | <0.5 | <0.5 |
| 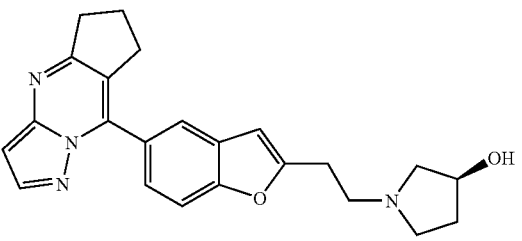 | 1-{2-[5-(6,7-Dihydro-5H-1,4,8a-triaza-s-indacen-8-yl)-benzofuran-2-yl]-ethyl}-pyrrolidin-3-(S)-ol | <0.5 | <0.05 |

| Structure | Chemical Name | Mouse H3 (μM) | Human H3 (μM) |
|---|---|---|---|
| 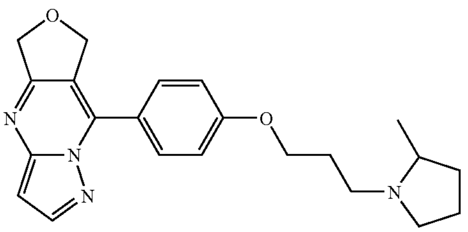 | 8-{4-[3-(2-Methyl-pyrrolidin-1-yl)-propoxy]-phenyl}-5H,7H-6-oxa-1,4,8a-triaza-s-indacene | <0.05 | <0.05 |

The invention claimed is:

1. A compound of the formula:

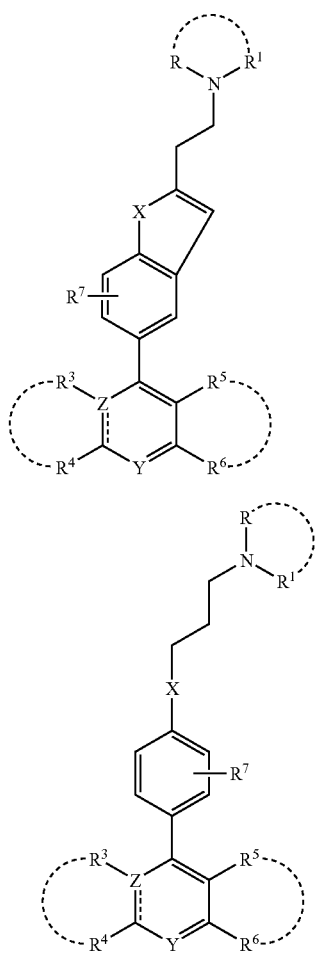

where X is O, S or CH$_2$;
Y is N;
Z is N;
R and R$^1$ are independently:
  (C1-C8) straight or branched alkyl optionally substituted with halogens or heteroatom groups, or
  (C3-C8) cycloalkyl substituted with halogens or heteroatom groups;

or
R and R$^1$ taken together form a cycloalkyl group optionally substituted with:
  (C1-C8) straight or branched alkyl;
  (C3-C8) cycloalkyl;
  halogens; or
  heteroatom groups; where one or more of the methylene groups may be replaced by O, N or S;
R$^3$ and R$^4$ taken together form:

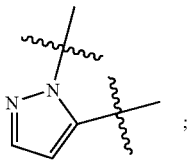

R$^5$ and R$^6$ taken together form —(CH$_2$)$_{3-5}$— and
R$^7$ is selected from the group consisting of H, halogen, alkyl, aryl, O-alkyl, S-alkyl, NH-alkyl, N(alkyl)$_2$, acyl and N-acyl,
or a pharmaceutically acceptable salt thereof.

2. A compound as in claim 1 where X is O, Y is N, Z is N, R and R$^1$ are —(CH$_2$)$_3$—, —CH$_2$—CH$_2$CH(CH$_3$)— or —CH$_2$CH$_2$OCH$_2$CH$_2$—, R$^3$ and R$^4$ are

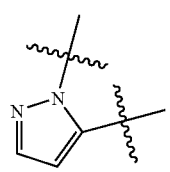

and R$^5$ and R$^6$ are —(CH$_2$)$_{3-5}$—, or —CH$_2$—CH$_2$CH(CH$_3$)—.

3. A compound of claim 1 selected from the group consisting of:
10-[4-(3-Piperidin-1-yl-propoxy)-phenyl]-6,7,8,9-tetrahydro-5H-1,4,10a-triaza-cyclohepta[f]indene;
10-{4-[3-(2-Methyl-pyrrolidin-1-yl)-propoxy]-phenyl}-6,7,8,9-tetrahydro-5H-1,4,10a-triaza-cyclohepta[f]indene;
Furan-2-ylmethyl-methyl-{3-[4-(6,7,8,9-tetrahydro-5H-1,4,10a-triaza-cyclohepta[f]inden-10-yl)-phenoxy]-propyl}-amine;
Diethyl-{3-[4-(6,7,8,9-tetrahydro-5H-1,4,10a-triaza-cyclohepta[f]inden-10-yl)-phenoxy]-propyl}-amine;

(2-Methoxy-ethyl)-{3-[4-(6,7,8,9-tetrahydro-5H-1,4,10a-triaza-cyclohepta[f]inden-10-yl)-phenoxy]-propyl}-amine;
10-[3-(3-Pyrrolidin-1-yl-propoxy)-phenyl]-6,7,8,9-tetrahydro-5H-1,4,10a-triaza-cyclohepta[f]indene;
(2-Methoxy-ethyl)-{3-[3-(6,7,8,9-tetrahydro-5H-1,4,10a-triaza-cyclohepta[f]inden-10-yl)-phenoxy]-propyl}-amine;
Furan-2-ylmethyl-{3-[3-(6,7,8,9,9a,10-hexahydro-5H-1,4,10a-triaza-cyclohepta[f]inden-10-yl)-phenoxy]-propyl}-methyl-amine;
Diethyl-{3-[3-(6,7,8,9-tetrahydro-5H-1,4,10a-triaza-cyclohepta[f]inden-10-yl)-phenoxy]-propyl}-amine;
10-[3-(3-Piperidin-1-yl-propoxy)-phenyl]-6,7,8,9-tetrahydro-5H-1,4,10a-triaza-cyclohepta[f]indene;
10-{3-[3-(2-Methyl-pyrrolidin-1-yl)-propoxy]-phenyl}-6,7,8,9-tetrahydro-5H-1,4,10a-triaza-cyclohepta[f]indene;
9-[4-(3-Pyrrolidin-1-yl-propoxy)-phenyl]-5,6,7,8-tetrahydro-pyrazolo[5,1-b]quinazoline;
9-[4-(3-Morpholin-4-yl-propoxy)-phenyl]-5,6,7,8-tetrahydro-pyrazolo[5,1-b]quinazoline;
Dimethyl-{3-[4-(5,6,7,8-tetrahydro-pyrazolo[5,1-b]quinazolin-9-yl)-phenoxy]-propyl}-amine;
9-[4-(3-Piperidin-1-yl-propoxy)-phenyl]-5,6,7,8-tetrahydro-pyrazolo[5,1-b]quinazoline;
9-{4-[3-(2-Methyl-pyrrolidin-1-yl)-propoxy]-phenyl}-5,6,7,8-tetrahydro-pyrazolo[5,1-b]quinazoline;
10-{4-[3-(2-Methyl-pyrrolidin-1-yl)-propoxy]-phenyl}-6,7,8,9-tetrahydro-5H-1,4,10a-triaza-cyclohepta[f]indene;
8-[4-(3-Pyrrolidin-1-yl-propoxy)-phenyl]-6,7-dihydro-5H-1,4,8a-triaza-s-indacene;
8-[4-(3-Morpholin-4-yl-propoxy)-phenyl]-6,7-dihydro-5H-1,4,8a-triaza-s-indacene;
{3-[4-(6,7-Dihydro-5H-1,4,8a-triaza-s-indacen-8-yl)-phenoxy]-propyl}-dimethyl-amine;
8-[4-(3-Piperidin-1-yl-propoxy)-phenyl]-6,7-dihydro-5H-1,4,8a-triaza-s-indacene;
8-{4-[3-(2-Methyl-pyrrolidin-1-yl)-propoxy]-phenyl}-6,7-dihydro-5H-1,4,8a-triaza-s-indacene;
10-{4-[3-(2,5-Dimethyl-pyrrolidin-1-yl)-propoxy]-phenyl}-6,7,8,9-tetrahydro-5H-1,4,10a-triaza-cyclohepta[f]indene;
9-{4-[3-(2-Methyl-pyrrolidin-1-yl)-propoxy]-phenyl}-5,6,7,8-tetrahydro-pyrazolo[5,1-b]quinazoline;
11-[4-(3-Pyrrolidin-1-yl-propoxy)-phenyl]-7,8,9,10-tetrahydro-6H-cyclohepta[b]quinoline;
9-[4-(3-Pyrrolidin-1-yl-propoxy)-phenyl]-1,2,3,4-tetrahydro-acridine;
9-{2-[2-(2-Methyl-pyrrolidin-1-yl)-ethyl]-benzofuran-5-yl}-5,6,7,8-tetrahydro-pyrazolo[5,1-b]quinazoline;
8-[2-(2-Pyrrolidin-1-yl-ethyl)-benzofuran-5-yl]-6,7-dihydro-5H-1,4,8a-triaza-s-indacene;
8-[2-(2-Morpholin-4-yl-ethyl)-benzofuran-5-yl]-6,7-dihydro-5H-1,4,8a-triaza-s-indacene;
8-[2-(2-Piperidin-1-yl-ethyl)-benzofuran-5-yl]-6,7-dihydro-5H-1,4,8a-triaza-s-indacene;
8-{2-[2-(2-Methyl-pyrrolidin-1-yl)-ethyl]-benzofuran-5-yl}-6,7-dihydro-5H-1,4,8a-triaza-s-indacene;
9-[2-(2-Piperidin-1-yl-ethyl)-benzofuran-5-yl]-5,6,7,8-tetrahydro-pyrazolo[5,1-b]quinazoline;
9-[2-(2-Morpholin-4-yl-ethyl)-benzofuran-5-yl]-5,6,7,8-tetrahydro-pyrazolo[5,1-b]quinazoline; and
9-{2-[2-(2-Methyl-pyrrolidin-1-yl)-ethyl]-benzofuran-5-yl}-5,6,7,8-tetrahydro-pyrazolo[5, 1-b]quinazoline.

4. A compound of claim 1 selected from the group consisting of:
9-[4-(3-Morpholin-4-yl-propoxy)-phenyl]-5,6,7,8-tetrahydro-pyrazolo[5,1-b]quinazoline;
10-{4-[3-(2-Methyl-pyrrolidin-1-yl)-propoxy]-phenyl}-6,7,8,9-tetrahydro-5H-1,4,10a-triaza-cyclohepta[f]indene;
8-[4-(3-Pyrrolidin-1-yl-propoxy)-phenyl]-6,7-dihydro-5H-1,4,8a-triaza-s-indacene;
8-[4-(3-Piperidin-1-yl-propoxy)-phenyl]-6,7-dihydro-5H-1,4,8a-triaza-s-indacene;
8-{4-[3-(2-(R)-Methyl-pyrrolidin-1-yl)-propoxy]-phenyl}-6,7-dihydro-5H-1,4,8a-triaza-s-indacene;
9-{4-[3-(2-(R)-Methyl-pyrrolidin-1-yl)-propoxy]-phenyl}-5,6,7,8-tetrahydro-pyrazolo[5,1-b]quinazoline;
9-[4-(3-Piperidin-1-yl)-propoxy]-phenyl]-5,6,7,8-tetrahydro-pyrazolo[5,1-b]quinazoline;
8-{4-[3-2-(R)-Methyl-pyrrolidin-1-yl)-propoxy]-phenyl}-5H,7H-6-oxa-1,4,8a-triaza-s-indacene; and
8-{4-[3-(2-Methyl-pyrrolidin-1-yl)-propoxy]-phenyl}-5H,7H-6-oxa-1,4,8a-tri-s-indacene.

5. A pharmaceutical composition comprising at least one compound of claim 1 in combination with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,319,103 B2 | Page 1 of 1 |
| APPLICATION NO. | : 11/170265 | |
| DATED | : January 15, 2008 | |
| INVENTOR(S) | : Bennani et al. | |

It is certified that error appears in the above-identified patent and that said Letters Patent is hereby corrected as shown below:

Column 56, line 41, delete "tri-s-indacene" and insert --triaza-s-indacene--.

Signed and Sealed this

Eleventh Day of November, 2008

JON W. DUDAS
*Director of the United States Patent and Trademark Office*